US012661063B2

(12) United States Patent
Stone et al.

(10) Patent No.: US 12,661,063 B2
(45) Date of Patent: Jun. 23, 2026

(54) INTRAOPERATIVE NEUROPHYSIOLOGICAL MONITORING SYSTEM

(71) Applicant: DEPUY SYNTHES PRODUCTS, INC., Raynham, MA (US)

(72) Inventors: Corbett Stone, San Diego, CA (US); Robin Vaughan, Escondido, CA (US); Kabir Gambhir, San Diego, CA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 332 days.

(21) Appl. No.: 17/217,159

(22) Filed: Mar. 30, 2021

(65) Prior Publication Data

US 2021/0282689 A1     Sep. 16, 2021

Related U.S. Application Data

(63) Continuation of application No. 15/917,904, filed on Mar. 12, 2018, now Pat. No. 10,980,438, which is a
(Continued)

(51) Int. Cl.
*A61B 5/00* (2006.01)
*A61B 5/395* (2021.01)
*A61N 1/36* (2006.01)

(52) U.S. Cl.
CPC ............ *A61B 5/4893* (2013.01); *A61B 5/395* (2021.01); *A61B 5/4821* (2013.01); *A61B 5/743* (2013.01);
(Continued)

(58) Field of Classification Search
CPC ...... A61B 5/389; A61B 5/4821; A61B 5/4893
See application file for complete search history.

(56) References Cited

U.S. PATENT DOCUMENTS 5,131,401 A * 7/1992 Westenskow ........ A61B 5/7207
600/595
5,284,154 A * 2/1994 Raymond ............ A61B 5/4893
600/587

(Continued)

FOREIGN PATENT DOCUMENTS

WO     WO2013067018 A2     5/2013

OTHER PUBLICATIONS

U.S. Appl. No. 61/554,486, filed Nov. 1, 2011.

*Primary Examiner* — Daniel L Cerioni
(74) *Attorney, Agent, or Firm* — Dunlap Codding, P.C.

(57)     ABSTRACT
An intraoperative neuromonitoring system for evaluating nerve function via a plurality of neural monitoring modalities includes an invasive medical instrument, a plurality of stimulating electrodes, a plurality of peripheral sensors, a patient module, and a control unit in communication with the patient module. The control unit is configured to maintain a range of acceptable values for each of a plurality of different neural monitoring modalities, determine, for each of the plurality of different neural monitoring modalities, whether the respective modality is within the range of acceptable values for that respective modality based on the indication of neuromuscular activity from one or more of the plurality of peripheral sensors, and provide an indication on a common screen displayed via the display, whether each respective neural monitoring modality is inside or outside of the range of acceptable values for that modality.

3 Claims, 24 Drawing Sheets

Related U.S. Application Data continuation of application No. 14/355,816, filed as application No. PCT/US2012/062809 on Oct. 31, 2012, now Pat. No. 9,949,651.

(60) Provisional application No. 61/554,486, filed on Nov. 1, 2011.

(52) U.S. Cl.
CPC ...... *A61N 1/36017* (2013.01); *A61B 2505/05* (2013.01)

(56) References Cited

U.S. PATENT DOCUMENTS

| | | | |
|---|---|---|---|
| 6,230,049 B1 * | 5/2001 | Fischell | A61B 5/372 |
| | | | 600/544 |
| 9,949,651 B2 | 4/2018 | Stone et al. | |
| 10,980,438 B2 | 4/2021 | Stone et al. | |
| 2004/0019370 A1 * | 1/2004 | Gliner | A61N 1/36017 |
| | | | 607/48 |
| 2004/0199084 A1 * | 10/2004 | Kelleher | A61B 5/24 |
| | | | 600/554 |
| 2005/0004623 A1 * | 1/2005 | Miles | A61B 5/4893 |
| | | | 607/48 |
| 2007/0016097 A1 * | 1/2007 | Farquhar | A61B 5/389 |
| | | | 606/32 |
| 2009/0177112 A1 * | 7/2009 | Gharib | A61B 5/4504 |
| | | | 600/554 |
| 2010/0152812 A1 * | 6/2010 | Flaherty | A61B 5/4041 |
| | | | 607/50 |
| 2010/0286554 A1 * | 11/2010 | Davis | A61B 5/24 |
| | | | 600/554 |
| 2011/0184308 A1 * | 7/2011 | Kaula | A61B 5/389 |
| | | | 600/546 |
| 2012/0095360 A1 * | 4/2012 | Runney | A61B 5/407 |
| | | | 600/554 |

* cited by examiner

298

308

299

314

INTRAOPERATIVE NEUROPHYSIOLOGICAL MONITORING SYSTEM

CROSS-REFERENCE TO RELATED APPLICATIONS

The present application is a continuation of U.S. patent application Ser. No. 15/917,904, filed on 12 Mar. 2018, and published as US 2018/0256051 (the '051 Application), which is a continuation of U.S. patent application Ser. No. 14/355,816, filed on May 1, 2014 and patented as U.S. Pat. No. 9,949,651 (the '651 Patent), which is the § 371 national stage entry of PCT/US2012/062809, filed Oct. 31, 2012 (the '809 Application), which claims the benefit of priority from U.S. Provisional Patent Application No. 61/554,486, filed on Nov. 1, 2011 (the '486 Application). Each of the '051 Application, the '651 Patent, the '809 Application, and the '486 Application are incorporated by reference in their entirety.

COPYRIGHT NOTICE

BACKGROUND

Intraoperative neurophysiological monitoring is a continually evolving field that aims to localize and monitor neural structures according to their functional basis within a human patient and, ultimately, it seeks to preserve the structural integrity of these neural structures during surgery or other invasive procedures. During spinal surgery for example, several neural structures may be placed at risk for potential injury—e.g., the spinal cord, one or more nerve roots, the lumbar plexus, and many (if not all) relevant vascular supply members going to and from the aforementioned elements.

Several electrophysiological modalities are currently available for monitoring various aspects of the central and peripheral nervous system during surgery or other invasive procedures in order to maintain their structural and/or functional integrity. Each neural monitoring modality offers a unique set of benefits and limitations as well as offering varying degrees of sensitivity or specificity as diagnostic techniques. For example, the most frequently used neural monitoring modalities for spinal procedures are SSEPs, MEPs, freerun or spontaneous EMG (sEMG), and triggered EMG (tEMG). In order to optimally preserve or protect the neural structures from structural or functional damage during spinal surgery, an interdisciplinary effort among the surgical, neuromonitoring, and neuroanesthesia teams is imperative.

Beyond the acquisition and communication of data required for intraoperative monitoring lies the art and science of interpreting the numerous permutations of results offered by multimodality intraoperative neuromonitoring, during a wide variety of spine surgeries. Oftentimes it is the interpretation and correlation of this data with particular structural or functionality impingements that is of the most benefit to the surgeon and, ultimately, the health of the patient. It has been found, however, that consistent and reliable interpretation of multiple modalities of information has been lacking and the structural and functional functioning of the patient's neural system has been impinged upon.

To that end, a need exists in the prior art for a neurophysiological monitoring system which monitors the neural pathology of a patient during an operation, interprets the data of multiple modalities of information being aggregated through such neural monitoring, and communicates such interpreted information to the surgeon and/or others in the operating chamber in a reliable and consistent manner. It is to such a neurophysiological monitoring system that the presently disclosed and claimed inventive concept(s), process(es), methodology(ies) and/or outcome(s) is directed.

BRIEF DESCRIPTION OF THE SEVERAL VIEWS OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, drawings, and appendices.

DETAILED DESCRIPTION

Figure 1:
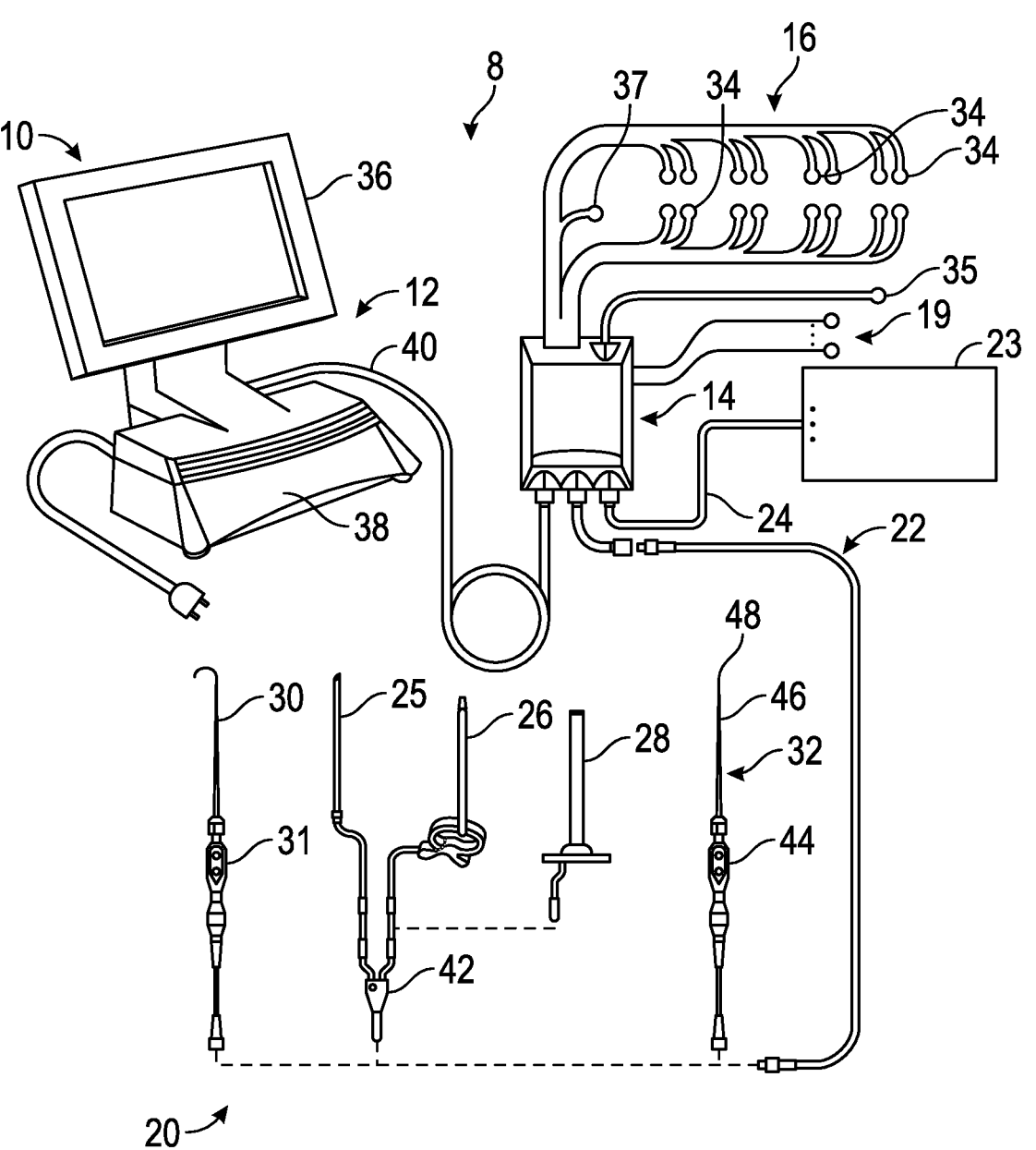
FIG. 1 is a perspective view of a surgical system for intraoperative neuromonitoring of at least one neural pathology throughout at least a portion of a surgical procedure according to the present disclosure.

Before explaining at least one embodiment of the inventive concept(s) disclosed herein in detail, it is to be understood that the presently disclosed and claimed inventive concept(s), process(es), methodology(ies) and/or outcome(s) is not limited in its application to the details of construction and the arrangement of the components or steps or methodologies set forth in the following description or illustrated in the drawings. The presently disclosed and claimed inventive concept(s), process(es), methodology(ies) and/or outcome(s) disclosed herein is capable of other embodiments or of being practiced or carried out in various ways. Also, it is to be understood that the phraseology and terminology employed herein is for the purpose of description and should not be regarded as limiting the presently disclosed and claimed inventive concept(s), process(es), methodology(ies) and/or outcome(s) herein in any way. With respect to any reference—patent or otherwise—mentioned herein, such reference should be considered to be incorporated by reference herein in its entirety as if set forth explicitly herein.

In the following detailed description of embodiments of the presently disclosed and claimed inventive concept(s), process(es), methodology(ies) and/or outcome(s), numerous specific details are set forth in order to provide a more thorough understanding of the presently disclosed and claimed inventive concept(s), process(es), methodology(ies) and/or outcome(s). However, it will be apparent to one of ordinary skill in the art that the presently disclosed and claimed inventive concept(s), process(es), methodology(ies) and/or outcome(s) within the disclosure may be practiced without one or more of these specific details, by skipping one or more of these specific details, or by modifying or transforming one or more these specific details in a manner that would be apparent to one of ordinary skill in the art given the present disclosure and teachings. In other instances, well-known features have not been described in detail to avoid unnecessarily complicating the instant disclosure and teachings and the following specification should be construed as including all relevant and/or known details or teachings that would be within the skill and knowledge of one of ordinary skill in the art.

The presently disclosed and claimed inventive concept(s), process(es), methodology(ies) and/or outcome(s) disclosed herein are generally directed to a neurophysiological monitoring system for use during spine surgery. The neurophysiological monitoring system is connected to the patient prior to spine surgery and permits a surgeon to monitor multiple neural monitoring modalities simultaneously during the entirety of the spine surgery—e.g., from patient positioning to final closure of the surgical wound or access point. The presently disclosed and taught neurophysiological monitoring system provides the surgeon with information regarding the status of various nerves or other neural structures within the patient as well as other information useful in obtaining a successful surgical outcome—e.g., positional information indicating the distance between one or more surgical accessories and one or more nerves which, when brought to the attention of the surgeon or other operating room participant, enhances the likelihood that the surgical accessories do not interfere (structurally or functionally) with one or more of the patient's nerves or other neural structures. The neurophysiological monitoring system will be described hereinafter in the context of spinal surgery utilizing a direct lateral approach to a patient's lumbar spine (i.e., 90 degrees to an anterior-posterior plane extending through a patient). However, it is to be understood, and would be understood by one of ordinary skill in the art given the present disclosure and teachings, that the presently disclosed and claimed inventive concept(s), process(es), methodology(ies) and/or outcome (s) are equally applicable to other types of surgeries, such as posterior-lateral spinal surgery, anterior-lateral spinal surgery, anterior spinal surgery, and posterior spinal surgery, for example.

As used herein, the terms "network-based," "cloud-based" and any variations thereof, are intended to cover the provision of configurable computational resources on demand via interfacing with a computer network, with software and/or data at least partially located on the computer network, by pooling the processing power of two or more networked processors, for example.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed.

As used herein the notation "a-n" appended to a reference numeral is intended as merely convenient shorthand to reference one, or more than one, and up to infinity, of the elements or features identified by the respective reference numeral (e.g., 134*a-n*). Similarly, a letter following a reference numeral is intended to reference an embodiment of the feature or element that may be similar, but not necessarily identical, to a previously described element or feature bearing the same reference numeral (e.g., 148, 148*a*, 148*b*, etc.). Such shorthand notations are used for purposes of clarity and convenience only, and should not be construed to limit the presently disclosed and claimed inventive concept(s), process(es), methodology(ies) and/or outcome(s) in any way, unless expressly stated to the contrary.

As used in the instant disclosure the terms "provide," "providing" and variations thereof as used herein comprise displaying, or providing for display, a screen either by one or more control units or to one or more control units by a host computer. The one or more control units may interface with a computer network and/or allow the one or more control units to obtain information from a host computer by sending and/or receiving digital and/or optical signals via a computer network interface (e.g. an Ethernet port, a TC/IP port, an optical port, a cable modem, and combinations thereof), for example.

Further, unless expressly stated to the contrary, "or" refers to an inclusive or and not to an exclusive use of the term "or." For example, a condition A or B is satisfied by anyone of the following: A is true (or present) and B is false (or not present), A is false (or not present) and B is true (or present), and both A and B are true (or present).

In addition, use of the term "a" or "an" are employed herein to describe elements and components of the embodiments herein. This is done merely for convenience and to give a general sense of the presently disclosed and claimed inventive concept(s), process(es), methodology(ies) and/or outcome(s). This description should be read to include one or at least one and the singular also includes the plural unless it is readily apparent to one of ordinary skill in the art that it is meant otherwise.

Finally, as used herein any reference to "one embodiment" or "an embodiment" means that a particular element, feature, structure, or characteristic described in connection with the embodiment is included in at least one embodiment of the presently disclosed and claimed inventive concept(s), process(es), methodology(ies) and/or outcome(s). The appearances of the phrase "in one embodiment" in various places in the specification do not necessarily refer to the same embodiment unless it would be readily apparent to one of ordinary skill in the art that it is meant otherwise.

Neural Monitoring Modalities

As one skilled in the art will understand and appreciate given the present disclosure and teaching(s), a variety of neural monitoring modalities exist to monitor and communicate (either audibly, visually, or a combination thereof) to one or more persons the structural or functional status or location of a nerve or other neural structure. The term "modality," as used herein, specifically refers to a physical agent which is applied to a patient in order to elicit a response from the patient wherein the response provides information that allows a surgeon, for example, to determine information relating to the structural or functional status of a patient's nerves or other neural structures. The physical agent can be in the form of electricity, energy from magnetic coils, or outside physical stimulus such as physically moving the patient or providing external force or movement, for example. The information elicited by the response can include, for example, the proximity of a nerve to a surgical access instrument or other device, the direction of a nerve relative to the placement of a surgical access instrument or other device, nerve pathology assessments such as the health or functional state of the nerve, or even the state of anesthesia that the patient is experiencing at the time of the application of the physical agent. As discussed below, the neurophysiological monitoring system may use a variety of different types of neural monitoring modalities such as somatosensory evoked potential, triggered electromyography, spontaneous electromyography, motor evoked potentials, train of fours (which may be referred to herein as a "twitch test") and nerve conduction velocity. Various types of neural monitoring modalities will be discussed hereinafter in more detail.

Somatosensory Evoked Potential

As used herein, the term "SSEP" stands for somatosensory evoked potential. Somatosensory evoked potentials provide monitoring of the dorsal column-medial lemniscus pathway, which mediates tactile discrimination, vibration sensation, form recognition, and joint/muscle sensation (conscious proprioception). Receptors in the skin, tendons, and muscles generate information that corresponds to these primary sensory modalities and relay these signals to neurons whose soma are located in dorsal root ganglia at all spinal levels. Axons from these first-order neurons project to the spinal cord via the medial root entry zone, giving rise to the fasciculi gracilis and cuneatus, which subsequently carry sensory information from the lower and upper extremities, respectively. The first synapse in this pathway occurs in the lower medulla after these tracts ascend via the dorsal columns in the spinal cord. Following a decussation that occurs at the medullary level, the medial lemniscus is formed; it ascends to the thalamus and ultimately relays sensory information to the primary somatosensory cortex (Brodmann areas 3, 1, and 2). Since SSEPs monitor the dorsal column-medial lemniscus pathway, standard patient sensory examination for tactile discrimination, vibration sensation, and joint/muscle sensation (conscious proprioception) is recommended prior to surgery, to document any deficits that may limit intraoperative neuromonitoring.

In the upper extremities, the median nerve (C-6, C-7, C-8, and T-1 roots) and ulnar nerve (C-8 and T-1) are frequently selected for monitoring, whereas the posterior tibial nerve (L-4, L-5, S-1, and S-2) and peroneal nerve (L-4, L-5, and S-1) are typically used in the lower extremities. Somatosensory evoked potentials involve electrical stimulation of mixed sensory and motor fibers caudal to the region of the spinal cord at risk, paired with recording of these signals rostral to the region at risk (typically at the dorsal neck and scalp). Electrical stimulation in the extremities produces major positive and negative deflections as signals ascend via the somatosensory pathway. Most often, a negative potential is measured at the scalp corresponding to the upper extremities at 20 milliseconds (N20), and a positive potential is measured at the scalp corresponding to the lower extremities at 37 milliseconds (P37). Additional subcortical waveforms can be obtained intraoperatively as the electrical volley propagates through the somatosensory pathway. A peripheral response recorded at the level of the brachial plexus (for the upper extremities) or the popliteal fossa (for the lower extremities) can be performed to ascertain adequacy of stimulation. These peripheral responses can also help to detect peripheral limb ischemia or nerve compression. It is important to note that in the case of SSEPs, these earlier peaks tend to be less sensitive to anesthesia, and can therefore frequently be used to differentiate SSEP monitoring changes resulting from anesthetic effects from those relating to surgical manipulation.

Alarm criteria of a 50% reduction in amplitude and/or a 10% increase in latency are generally used as guidelines for notifying the surgeon of a potential deficit, and corrective intervention should be considered if these changes correspond to a particular surgical manipulation. Factors that potentially affect the SSEP amplitude include halogenated agents, nitrous oxide, hypothermia, hypotension, and electrical interference. A common factor affecting SSEP latency readings is temperature. Any SSEP changes with amplitude reduction of more than 50% should also be considered relevant if they are temporally associated with a specific surgical intervention, such as during placement of spinal instrumentation or during correction of a spinal deformity.

Although SSEP signals are good basic indicators of spinal cord function, less information is provided regarding nerve root function. Somatosensory evoked potentials are a composite of summated neural signals that enter the spinal cord through multiple segments. In addition, due to central amplification, it is possible for SSEPs to remain completely normal in the face of a nerve root injury.

Motor Evoked Potentials

As used herein, the term "MEP" refers to Motor Evoked Potentials. Motor evoked potentials (MEP) are recorded from muscles following direct stimulation of exposed motor cortex, or transcranial stimulation of motor cortex, either magnetic or electrical. Transcranial magnetic MEP (TCm-MEP) potentially offer clinical diagnostic applications.

Transcranial electrical MEP (TCeMEP) has been used widely for intraoperative monitoring of pyramidal tract functional integrity and would be understood readily by one of ordinary skill in the art.

For standard transcranial MEP recording (TcMEP), stimulation electrodes are placed at C3 and C4 (10-10 according to the International System of indication) for activation of both upper and lower extremity muscle groups, with alternative sites at C1 and C2 if more focal activation of the lower extremity muscle groups is desired. Establishing a patient setup with multiple sites available for stimulation is recommended, especially in patients with myelopathy, given the greater difficulty in obtaining MEP recordings. The stimulation intensity alters the current field size and distribution to the cortex and subcortical fibers. Increasing stimulation intensity correlates with greater axonal recruitment and spatial summation along with bilateral stimulation. Subcortical white matter motor tracts are activated at the bend of the axon exiting the gray matter, or entering the internal capsule or even brainstem, which is not an issue when the structures at risk are located below the foramen magnum, as is the case in spine surgery. Stimulation trains increase temporal summation at the α-motoneurons, leading to a higher likelihood of achieving a stimulus threshold. Stimulation rates>200 Hz are typically required for temporal summation at motoneurons. Latencies of 20 msec in the hand and 45 msec in the foot are typically observed, depending on various factors such as the underlying pathological condition, the patient's height, and body temperature.

There are a variety of methods utilized for the interpretation of MEPs. For example, four methods are routinely used for interpretation for TcMEP responses: 1) the all-or-nothing criterion, 2) the amplitude criterion, 3) the threshold criterion, and 4) the morphology criterion. The all-or-nothing criterion may be the most widely cited and used method, given the inherent variability of signals in MEP monitoring. Based on this approach, a complete loss of the MEP signal from a preliminary baseline recording is indicative of a clinically significant event. A modification of the all-or-nothing approach involves measuring the CMAP ("compound muscle action potential") amplitude at baseline, then measuring relative changes in amplitude to determine if a clinically significant change has occurred. For example, an 80% amplitude decrement in at least 1 out of 6 recording sites may be used as a criterion for a clinically significant change. A similar form of reasoning can be applied to the threshold criterion, which analyzes the increases in stimulation threshold required to maintain CMAP responses. Lastly, the morphology criterion looks at impaired motor conduction of the corticospinal tracts by tracking changes in the pattern and duration of MEP waveform morphology. Factors that may alter MEP waveform morphological characteristics include anesthetic fade, body temperature, blood pressure, surgical positioning, and technical pitfalls, among others.

Although MEPs have become commonplace for neuromonitoring of the motor tracts, there are some disadvantages to MEP monitoring. Primary among the many drawbacks of MEP monitoring is the inability of MEP to perform continuous monitoring (which can be accomplished with SSEPs), requiring that MEPs be obtained intermittently at given intervals during the surgery. Another inherent limitation of monitoring MEP signals is that they may be more technically challenging to obtain and/or properly interpreting the signals during complicated surgical procedures.

Spontaneous Electromyography

As used herein, sEMG refers to "spontaneous electro-myography" (also generally known in the art as "free run" electromyography) which can be used to intraoperatively monitor the corresponding nerve roots responsible for muscle innervation. This spontaneous motor activity can be measured with recording electrodes placed in the muscles of interest and based on the structures at risk. Although no stimulation is performed for this technique, surgical manipulation such as pulling, stretching, or compression of nerves produces neurotonic discharges resulting in activity in the corresponding innervated muscle(s). Specific muscles are normally paired with single nerve roots, yet in reality some redundancy in innervation occurs, and muscle selection is made to maximize coverage based on the spinal level of interest to the surgeon. During cervical spine procedures, the C-5 nerve root is at particular risk of injury and requires particular attention in monitoring. For this reason, concurrent monitoring of 2 muscles is oftentimes recommended to minimize the risk of C-5 nerve root injury. The deltoid (predominantly C-5, also C-6) and biceps brachii (predominantly C-6, also C-5) muscles may be used to monitor the C-5 level. Spontaneous EMG tends to be quite sensitive to irritation of the nerve root due to retraction, irrigation, and manipulation during surgery.

Triggered Electromyography

Over the past 20 years, segmental instrumentation and fusion using pedicle screw constructs have become the standard for spinal stabilization. A potentially preventable risk of pedicle screw placement is a medial screw breach of the pedicle wall into the spinal canal. Triggered EMG is a method that can be used to determine whether screws have breached the medial or inferior pedicle wall and thus pose a risk to the exiting nerve root at that level. When a pedicle screw is accurately placed, the surrounding bone acts as an insulator to electrical conduction, and a higher amount of electrical current is thus required to stimulate the surrounding nerve root. Typically, a monopolar electrode is used to directly stimulate the top of the pedicle screw at increasing current intensities. Needle electrodes in the appropriate muscle groups measure CMAP time locked to the stimulation. In order to ensure that the stimulus current is delivered correctly, direct nerve root stimulation using <2 mA can be attempted to ensure a CMAP response in the appropriate distal muscle group and thereby confirm the delivery or application of the stimulus current.

When a medial pedicle wall breach occurs, the stimulation threshold is significantly reduced. Due to the variation in thickness and shape between thoracic and lumbar pedicles, different stimulation thresholds exist for these regions. Earlier studies have demonstrated that a threshold<10 mA for screw stimulation, or 7 mA for probe stimulation, suggest a medial wall breach in the lumbar pedicles. A threshold response between 10 and 20 mA gives a reasonable probability that no of breach of the medial wall has occurred, whereas thresholds>15 mA indicate a 98% likelihood of accurate screw positioning on postoperative CT scan. Thresholds above 20 mA assure a strong probability that there is no breach of the medial pedicle wall. For thoracic pedicle screw placement, stimulation thresholds<6 mA suggest a medial pedicle breach.

During pedicle screw stimulation, false-negative responses can occur as a result of various factors, including the use of muscles relaxants, current spread, or preexisting nerve damage. The degree of muscle relaxation can be measured using a train-of-4 test. Just as in the case of sEMG monitoring, tEMG monitoring requires that no paralytics be used and that 4 of 4 twitches are optimal for reliable recording. Special attention should to be paid to fluid, blood, or soft tissue around the head of the screw at the time of stimulation that could potentially shunt current away from the screw. Furthermore, it is important that the stimulation probe be placed directly on the top of the screw and not the tulip, as these 2 structures are not structurally fused and therefore do not conduct current as a single unit. Once the probe is placed on the screw, current will ideally flow from the screw to an appropriately placed reference electrode in the paraspinal muscles on the contralateral side. A third possible reason for false-negative thresholds is the presence of preexisting nerve root injury. Injured nerve roots will have higher triggering thresholds, with literature reports ranging from 6 to >10 mA for a chronically compressed root, as compared with 2 mA for a normal nerve root. In nerve roots where there is known or suspected damage, direct nerve root threshold testing is valuable to establish a baseline value.

Train of Fours

A train of fours analysis can be utilized to quantify the amount of paralytic in a patient to determine a state of anesthesia that the patient is experiencing at the time of testing. In a train of fours analysis, four electrical stimuli are typically presented to the patient's peripheral nerves resulting in four twitches in the corresponding muscle groups. The strength of the muscle twitches corresponds to the quantity/amount of paralytic within the patient. In other words, an amplitude of the response correlates to a level of the patient's paralysis. As will be discussed in more detail below, a train of fours analysis is preferably performed prior to every major surgical event so that the surgeon will be informed of the patient's level of paralysis or level of anesthesia. When the surgery is directed to the patient's spine, common major surgical events include access, dilation, retraction, and the like.

Nerve Conduction Velocity

Nerve conduction velocity (NCV) is a test to determine how "fast" electrical signals are capable of moving through a nerve at the time of testing. The nerve conduction velocity test is implemented by attaching surface electrodes on the skin over nerves at various locations. Each surface electrode gives off a very mild electrical impulse, which stimulates the nerve. The nerve's resulting electrical activity is thereafter recorded by the other electrodes. The distance between electrodes and the time it takes for electrical impulses to travel between electrodes is used to determine the speed of the nerve signals. It should be noted that electromyography (recording from needles placed into the muscles) may be performed at the same time as nerve conduction velocity tests.

NCV may involve the stimulation of peripheral nerves using surface electrodes placed along a nerve path within a patient. In particular, stimulating and recording electrodes may be placed along the nerve path, in addition to a ground electrode placed nearby. The recording electrode, placed along the nerve path, may be placed on the nerve path as it leads proximally away from a limb. The electrodes placed on the patient may be measured to correlate the time of nerve conduction into a velocity measurement. NCV may differ from patient to patient, but may be in the range of 45-55 meters per second. The determination of amplitude and latency may also be used during NCV measurements. Nerve health monitoring via NCV may be used in addition to other nerve monitoring procedures during the creation and maintenance of a spinal access corridor, during a spinal surgery, whether from an anterior, posterior, anterolateral, posterolateral, or lateral approach.

NCV may compliment triggered and running EMG measurements. While EMG primarily measures motor nerve activity, NCV primarily measures sensory nerve activity. NCV may be utilized to measure conduction in either direction along the nerve's path, orthodromic or antidromic. During a spinal access surgical procedure, EMG may measure the direct stimulation of a nerve or nerve root that is accessible in the surgical field, with a mono or bipolar probe. Stimulus evoked CMAPs (Compound Muscle Action Potentials) which appear normal may demonstrate integrity of the functional nerve muscle unit. If a root or nerve supplying a monitored myotome is manipulated during the surgical procedure, the muscle discharges and resultant motor unit potentials may be recorded. These potentials quickly diminish. If a nerve is severed, loses its ability to discharge due to traction, compression, or ischemia, EMG may lose diagnostic value. In such cases, NCV may better indicate a nerve's health. NCV may also be used to verify a nerve's health if the desired outcome is to relieve a pinched nerve via decompression or surgical intervention. Further, NCV measurements may not be affected by general anesthesia and neuromuscular blocking agents, as opposed to EMG which may not be possible with complete neuromuscular blocking.

NCV may be used to measure the nerve conduction of motor nerves and sensory nerves. Motor nerve conduction velocity (mNCV) measurement may be measured by transcranial stimulation, with a nerve path extending, for example, from the brain to spinal cord to lumbar plexus to retractor. It may be necessary to record baseline data as NCV measurements are patient specific due to changes in patient height, weight, age, etc. Sensory nerve conduction velocity (sNCV) measurement may be measured by stimulating a peripheral nerve at around 25 mA at about 4-5 Hz, with a nerve path which may be from a limb to lumbar plexus to retractor. As with mNCV, it may be necessary to record baseline data as the sNCV measurements are patient specific due to changes in patient height, weight, age, etc. The mNCV and sNCV measurements can verify nerve traction, compression, ischemia, or impairment in motor nerves and sensory nerves, respectively. If any significant NCV change is presented, the NCV change may indicate temporary nerve impairment that may be alleviated by repositioning of the surgical access instrument impinging the nerve during surgery.

As will be appreciated by one of ordinary skill in the art provided the teachings and disclosure herein, various additional modalities may be incorporated within the surgical system disclosed and claimed herein. For example, but not by way of limitation, mechanomyography (MMG) may be employed as one such neural monitoring modality. MMG systems function by measuring the mechanical response of a muscle following nerve stimulation, compared to traditional techniques that monitor the electrical response of muscle using EMG. MMG has been widely used in laboratory settings to study things such as muscle fatigue and, given the present disclosure, one of ordinary skill in the art will appreciate that MMG can be applied as an intraoperative tool for locating nerves. MMG is effective for detecting the presence of nerves or other neural structures during surgery—particularly with regards to minimally invasive surgical procedures—where the nerves or other neural structures cannot be directly visualized. Since EMG systems monitor for small changes in muscle electrical activity, there is the potential for electrical interference when using EMG in certain circumstances. By using MMG, alone or in combination with EMG or other modalities, electrical interference issues are minimized or can be ignored since any response of the muscles to the electrical stimulation is measured through mechanical sensors such as accelerometers, for example but not by way of limitation. MMG may also provide faster response rates thereby indicating a higher sensitivity for detection of nerves at a lower threshold. Further, muscle response to electrical stimulus varies with the distance of the nerve from the source of the stimulus: i.e., by working with different levels of current, a relationship between the current and distance is known thereby allowing the surgeon to determine precisely how far a nerve is from the stimulus probe. In recent studies, MMG detected the presence of a nerve on average 1.2 seconds earlier than EMG, using approximately half the amount of stimulating current. Since electrical resistance is highly variable, depending on the conducting tissue, EMG may require currents as high as 200 mA while MMG in similar tissue would only require, for example, a maximum current output of 6 mA.

Given the preceding—as well as the knowledge known—one of ordinary skill in the art would appreciate that a surgical system could incorporate one, two, three and up to an infinite number of different neural monitoring modalities capable of employing nerve proximity, nerve direction, and nerve pathology assessments according to the presently disclosed and claimed inventive concept(s), process(es), methodology(ies) and/or outcome(s). It should be understood that the number of neural monitoring modalities used and communicated to a surgeon or other operating room personnel (e.g., by visual, aural or olfactory indicia) are not limited to a single neural monitoring modality at any one particular time. Rather, one or more indicia can be communicated at any given time—for example, EMG and NCV data may be communicated to the surgeon or other operating room personnel at the same time. Furthermore, all of the modalities may be communicated at the same time. As will be even more apparent in light of the information below, the presently disclosed and claimed inventive concept(s), process(es), methodology(ies) and/or outcome(s) encompass all such variations of neural monitoring modalities being represented to the surgeon or other operating room personnel.

Description of Surgical System

FIG. 1 illustrates, by way of example only, a neurophysiological monitoring system 8 having a surgical system 10 capable of employing nerve proximity, nerve direction, and nerve pathology assessments according to the presently disclosed and claimed inventive concept(s), process(es), methodology(ies) and/or outcome(s). As will be explained in greater detail below, the surgical system 10 is capable of providing safe and reproducible access to any number of surgical target sites, and well as monitoring changes in nerve pathology (health or status) during surgical procedures. It is expressly noted that, although described herein largely in terms of use in spinal surgery, the surgical system 10 and related methods of the presently disclosed and claimed inventive concept(s), process(es), methodology(ies) and/or outcome(s) are suitable for use in any number of additional surgical procedures wherein tissue having significant neural structures must be passed through (or near) in order to establish an operative corridor, or where neural structures are retracted or otherwise impinged upon by surgical access instruments such as dilators, retractors and the like.

Figure 2:
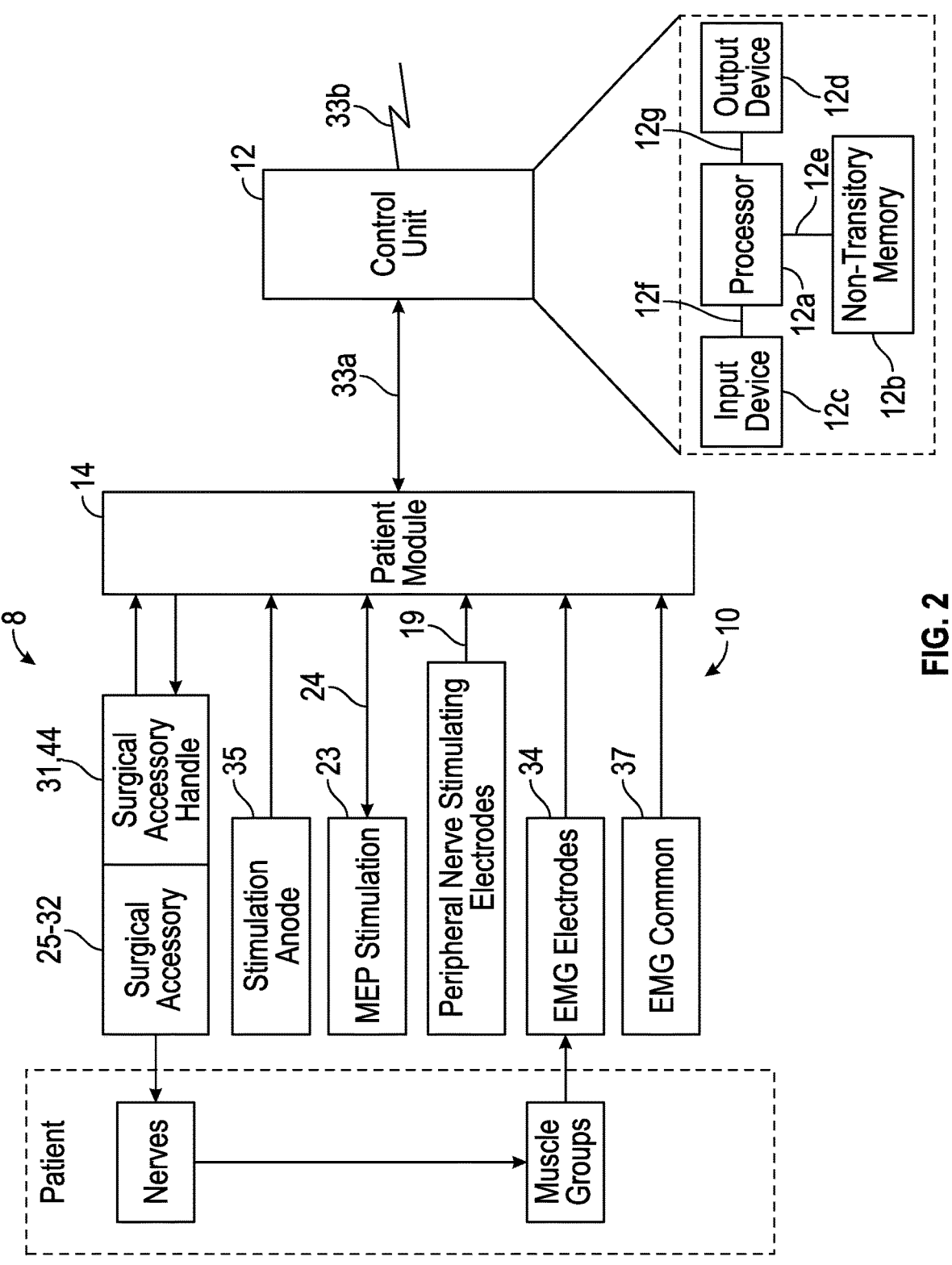
FIG. 2 is a block diagram of the surgical system shown in FIG. 1.

The surgical system 10 includes a control unit 12, a patient module 14, an EMG harness 16, a return electrode 18 coupled to the patient module 14, a plurality of peripheral nerve stimulation electrodes 19, a host of surgical accessories 20 capable of being coupled to the patient module 14 via one or more accessory cables 22, and a multiple purpose unit 23 capable of carrying out multiple modalities of stimulation shown in FIG. 1 for example, but not by way of limitation, multiple purpose unit 23 may be an evoked potential stimulator 23 connected to the patient module 14 via one or more accessory cables 24. The surgical accessories 20 may include, but are not necessarily limited to, surgical access components (such as a K-wire 25, one or more dilators 26, and a working dilator 28), neural pathology monitoring devices (such as nerve root retractor 30), and devices for performing pedicle screw test (such as screw test probe 32). A block diagram of the surgical system 10 is shown in FIG. 2, the operation of which is readily apparent to one of ordinary skill in the art in view of the following description. The one or more patient module 14 can be a separate component that is external to the base 38 of the control unit 12, or within the base 38 of the control unit 12.

The control unit 12 comprises one or more processors 12a capable of executing processor executable code, one or more non-transitory memory 12b capable of storing processor executable code, an input device 12c, and an output device 12d, all of which can be stand-alone, partially or completely network-based or cloud-based, and not necessarily located in a single physical location.

The one or more processors 12a can be implemented as a single processor 12a or multiple processors 12a working together to execute the logic described herein. Exemplary embodiments of the one or more processor 12a include a digital signal processor (DSP), a central processing unit (CPU), a field programmable gate array (FPGA), a microprocessor, a multi-core processor, and combinations thereof. The one or more processor 12a is capable of communicating with the one or more memories 12b via a path 12e which can be implemented as a data bus, for example. The one or more processor 12a is capable of communicating with the input device 12c and the output device 12d via paths 12f and 12g, respectively. Paths 12f and 12g may be implemented similarly to, or differently from, path 12e. The one or more processor 12a is further capable of interfacing and/or communicating with the one or more patient modules 14 via a network 33, such as by exchanging electronic, digital and/or optical signals via one or more physical or virtual ports using a network protocol such as TCP/IP, for example. The network 33 can also be implemented with a serial and/or parallel cable utilizing any suitable protocol. It is to be understood that in certain embodiments using more than one processor 12a, the one or more processor(s) 12a may be located remotely from one another, located in the same location, or comprising a unitary multi-core processor (not shown). The one or more processor 12a is capable of reading and/or executing processor executable code and/or or creating, manipulating, altering, and storing computer data structures into the one or more memory 12b.

The one or more memory 12b stores processor executable code for causing the one or more processor 12a to implement the functions described herein. The one or more memory 12b may be implemented as any conventional non-transitory memory 12b, such as random access memory (RAM), a CD-ROM, a hard drive, a solid state drive, a flash drive, a memory card, a DVD-ROM, a floppy disk, an optical drive, a compact flash drive, holographic drives, and combinations thereof, for example. It is to be understood that while one or more memory 12b is shown located in the same physical location as the processor 12a, the one or more memory 12b may be located remotely from the processor 12a and may communicate with the one or more processor 12a via the network 33a, or a network 33b. Additionally, when more than one memory 12b is used, one or more memory 12b may be located in the same physical location as the processor 12a, and one or more memory 12b may be located in a remote physical location from the processor 12a. The physical location(s) of the one or more memory 12b can be varied, and the one or more memory 12b may be implemented as a "cloud memory" i. e., one or more memory 12b which is partially, or completely based on or accessed using the networks 33a or 33b.

The input device 12c transmits data to the processor 12a, and can be implemented as a keyboard, a mouse, a touchscreen, a camera, a cellular phone, a tablet, a smart phone, a PDA, a microphone, a network adapter, a probe having a sensor therein, a microcapillary testing device or array, a microfluidic testing device, and combinations thereof, for example but not by way of limitation. Any device capable of functionally transmitting data to the processor 12a can be used as the input device 12c. The input device 12c may be located in the same physical location as the control unit 12, or may be remotely located and/or partially or completely network-based. The input device 12c communicates with the processor 12a via path 12f.

The output device 12d transmits information from the processor 12a to a user, such that the information can be perceived by the user. For example but not by way of limitation, the output device 12d can be implemented as a server, a computer monitor, a cell phone, a tablet, a speaker, a website, a PDA, a fax, a printer, a projector, a laptop monitor, and combinations thereof. The output device 12d can be physically co-located with the processor 12a, or can be located remotely from the processor 12a, and may be partially or completely network based (e.g., a website). The output device 12d communicates with the processor 12a via the path 12g. As used herein, the term "user" is not limited to a human, and may comprise a human using a computer, a host system, a smart phone, a tablet, a computerized pen or writing device, and combinations thereof, for example but not by way of limitation.

In one embodiment, the control unit 12 includes a touch screen display 36 and a base 38. In this embodiment, the touch screen display 36 forms the input device 12c and the output device 12d. The touch screen display 36 is preferably equipped with a graphical user interface (GUI) capable of communicating information to the user and receiving instructions from the user. The base 38 preferably forms a housing containing computer hardware and software implementing the processor 12a and the non-transitory memory 12b to control the stimulation sources, receive digitized signals and other information from the patient module 14, and processes the neural monitoring modalities, such as an electro-myocardial graph, to extract characteristic information for each muscle group, and displays the processed data to the operator via the touch screen display 36. The primary functions of the software stored on the one or more memory 12b of the control unit 12 include receiving user commands via the touch screen display 36, activating stimulation in a requested mode of the available surgery modes (e.g., baseline, positioning, approach, access, dissecting, trial/insertion and supplemental fixation), processing signal data according to defined algorithms stored on the memory 12b, displaying received parameters and processed data, and monitoring system status and reporting fault conditions.

The patient module 14 is connected to the control unit 12 via the network 33a which may be a parallel or serial cable and contains the electrical connections to all electrodes, signal conditioning circuitry, stimulator drive and steering circuitry, and a digital communications interface to the control unit 12. In use, the control unit 12 may be situated outside but close to the surgical field (such as on a cart adjacent the operating table) such that the touch screen display 36 is directed towards the surgeon for easy visualization. The patient module 14 may be located between the patient's legs, or may be affixed to the end of the operating table at mid-leg level using a bedrail clamp. The position selected should be such that the leads can reach their farthest desired location without tension during the surgical procedure.

Figure 3:
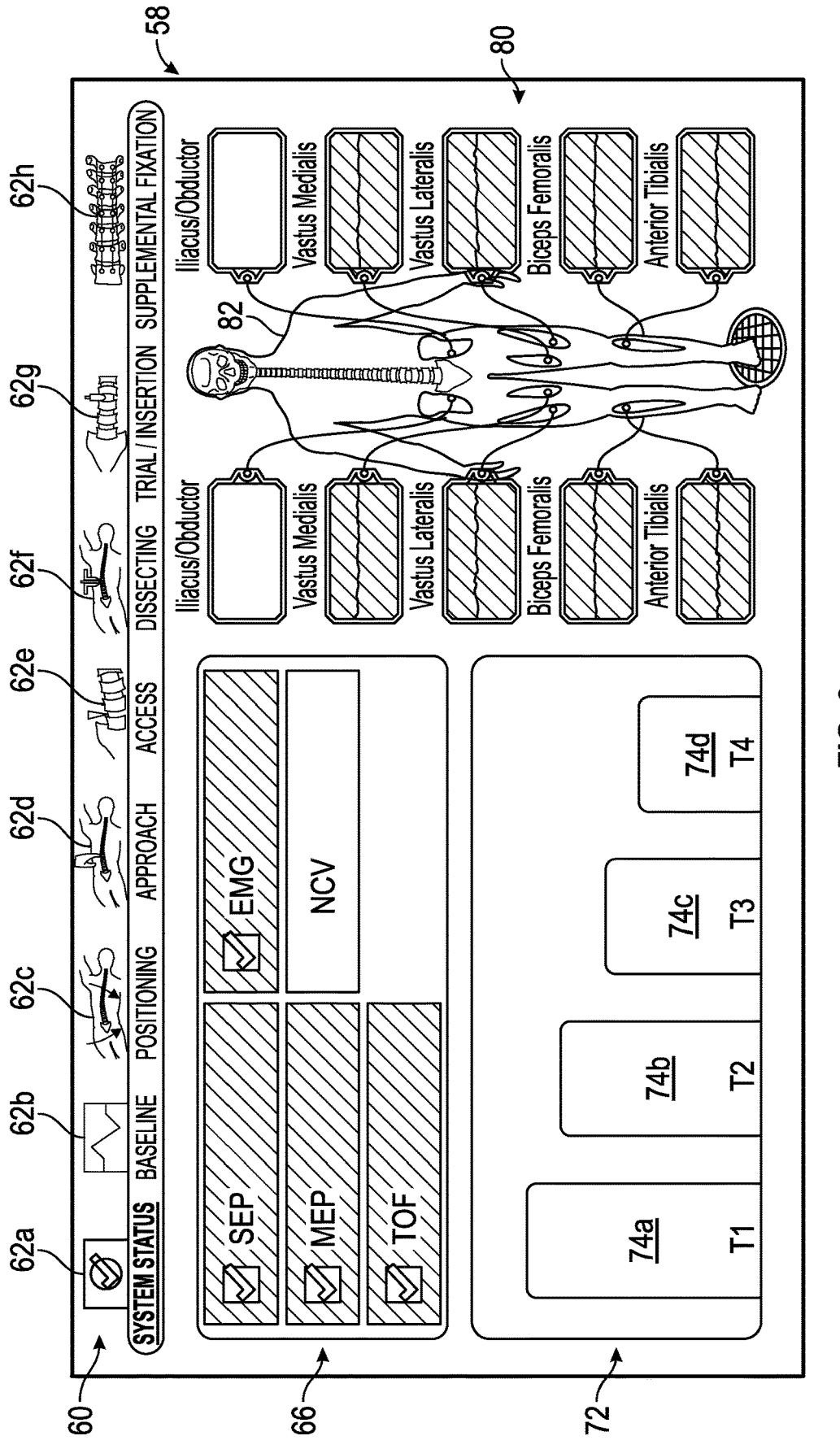
FIG. 3 shows an exemplary status screen generated by the control unit of the surgical system of FIG. 1 in accordance with the presently disclosed concepts.

FIGS. 3-16 show exemplary embodiments of status screens generated by a control unit of the surgical system of FIG. 1 in which multiple neural monitoring modalities are simultaneously being monitored in accordance with the present disclosure. Referring now to FIG. 3, the information displayed to the user on touch screen display 36 may include, but is not necessarily limited to, alpha-numeric and/or graphical information regarding nerve proximity, nerve direction, nerve pathology, stimulation level, myotome/EMG levels, screw testing, advance or hold instructions, the instrument in use and a level of the patient's paralysis. Shown in FIG. 3 is a system status screen 58 displayed, for example, when the surgeon system 10 has been placed into the system status mode. In one embodiment (set forth by way of example only) the system status screen 58 provided by the touch screen display 36 includes the following components:

1) a mode section 60 including a plurality of interfaces 62*a-h* that can be selected by a user to place the surgeon's system 10 in a variety of predetermined modes. The predetermined modes can vary and are shown by way of example in a situation where the surgeon's system 10 is used for a direct lateral approach to the patient's lumbar spine. In this example, the predetermined modes include a status mode, a baseline mode, a positioning mode, an approach mode, an access mode, a dissecting mode, a trial/insertion mode and a supplemental fixation mode. Depending upon the mode, the interface 62*a-h* may include an identification of the surgical accessory 20 to be used in the mode, such as the surgical access components (K-Wire, Dilators, Working Dilator), nerve pathology monitoring device (Nerve Root Retractor), and/or screw test device (Screw Test Probe) depending on which is attached.

2) a status summary section 66 including a plurality of zones indicating a current status for each of the neural monitoring modalities, which in the example shown in FIG. 3 includes SSEP, MEP, TOF, EMG and NCV. In general, the current status can vary, but in an embodiment, the current status can either be within a predetermined range that is considered acceptable, unacceptable or on the peripheries of these areas and thus constitutes a warning zone indicating that the user should be cautious in preceding with the task being undertaken. The current status can be communicated in a variety of ways, such as by changing colors of the zones, flashing lights, voice prompts or audio warnings, pleasant or noxious smells, or the like. In a one embodiment, the color green is utilized to communicate that the status is within a predetermined range of acceptability, the color red is utilized to communicate that the status is within a predetermined range of unacceptability, and the color yellow is utilized to communicate that the status is within a predetermined range indicating that a warning is necessary.

3) an anesthetic status section 72 providing a status of the patient's paralysis. Data regarding the status of the patient's paralysis can be determined utilizing a train of four analysis, for example, having four sensors connected to the patient's nerves as discussed above. For this reason, the anesthetic status section 72 may be referred to herein as a train of four status. In the example shown, the anesthetic status section 72 includes separate zones 74*a*, 74*b*, 74*c* and 74*d* with one of the zones for the sensors connected to the patient's nerves. As shown, each of the zones 74*a*, 74*b*, 74*c* and 74*d* may show a magnitude of twitch generated by the electrical signals used in the train of four analysis.

4) a monitoring location status section 80 providing an image 82 of a human body/skeleton showing the electrode placement on the body, nerves upon which the electrodes are placed and EMG status 84*a-j* of waveforms being sensed by the electrodes. Exemplary nerves that may be monitored by EMG and indicated in status 84*a-j* include Iliacus/Obductor, Vastus Medialis, Vastus Lateralis, Biceps Femoralis, and Anterior Tibialis, for example but not by way of limitation.

The surgical system 10 accomplishes safe and reproducible access to a surgical target site by detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. The surgical system 10 does so by electrically stimulating nerves via one or more stimulation electrodes at the distal end of the surgical access components 25-28 while monitoring the EMG responses of the muscle groups innervated by the nerves. In one embodiment, this is accomplished via 8 pairs of EMG electrodes 34 placed on the skin over the major muscle groups on the legs (four per side), an anode electrode 35 providing a return path for the stimulation current, and a common electrode 37 providing a ground reference to pre-amplifiers in the patient module 14.

In use, all appropriate electrodes including the return electrode 18, peripheral nerve stimulation electrodes 19, motor evoked potential stimulator 23, EMG electrodes 34, the anode electrode 35 and the common electrode 37 are applied to the patient prior to positioning. The patient is positioned in a lateral decubitus position, and then a correct operative level and incision location is located, preferably with fluoroscopic views, and thereafter a skin incision targeting an interior third of an intravertebral disc space is made. However, a longitudinal incision may be used if multiple levels will be fused, for example.

Once the skin incision is made and the subcutaneous tissue is taken down, the oblique muscles of the abdomen should be visible. The surgical access components 25-28 are designed to bluntly dissect the tissue between the patient's skin and the surgical target site through the oblique muscles, the retroperitoneal space, and the psoas muscle to form the operative corridor to the patient's spine. The operative corridor is formed by advancing the K-wire 25, or an initial dilator 26, towards the target site, preferably after having been aligned using any number of commercially available surgical guide frames. The K-wire 25 and/or the initial dilator 26 can be provided with one or more stimulating electrodes that emit electricity in order to aid in determining the position of the K-wire 25 and/or the initial dilator 26 relative to one or more of the patient's nerves and/or other neural structures.

An obturator (not shown) may be included inside the initial dilator 26 and may similarly be equipped with one or more stimulating electrodes. Once the proper location is achieved, the obturator (not shown) may be removed and the K-wire 25 inserted down the center of the initial dilator 26 and docked to the given surgical target site, such as the annulus of an intervertebral disc. Dilators of increasing diameter are then guided over the previously installed dilator 26 until the desired lumen is installed. By way of example only, the dilators 26 may range in diameter from 6 mm to 30 mm. In one embodiment, each dilator 26 has a stimulating electrode at the tip to allow detection and direction evaluation, as will be described below. In another embodiment, each dilator 26 may have more than one stimulating electrode placed at the tip or along the side of each of the dilators 26. The working dilator 28 is installed over the last dilator 26 and then all the dilators 26 are removed from inside the inner lumen of the working dilator 28 to establish the operative corridor therethrough.

A stimulator driver 42 is provided to electrically couple the particular surgical access component 25-28 to the patient module 14 (via accessory cable 22). In one embodiment, the stimulator driver 42 includes one or more buttons for selectively activating the stimulation current and/or directing it to a particular surgical access component.

The surgical system 10 accomplishes neural pathology monitoring by electrically stimulating a retracted nerve root via one or more stimulation electrodes at the distal end of the nerve root retractor 30 while monitoring the EMG responses of the muscle group innervated by the particular nerve. The EMG responses provide a quantitative measure of the nerve depolarization caused by the electrical stimulus.

Analysis of the EMG responses may then be used to assess the degree to which retraction of a nerve or other neural structure affects the nerve function over time, as will be described with greater particularity below. One advantage of such monitoring, by way of example only, is that the conduction of the nerve may be monitored during the procedure to determine whether the neurophysiology and/or function of the nerve changes (for the better or worse) as the result of the particular surgical procedure. For example, it may be observed that the nerve conduction increases as the result of the operation, indicating that the previously inhibited nerve has been positively affected by the operation. The nerve root retractor 30 may comprise any number of suitable devices capable of maintaining contact with a nerve or nerve root. The nerve root retractor 30 may be dimensioned in any number of different fashions, including having a generally curved distal region (shown as a side view in FIG. 1 to illustrate the concave region where the nerve will be positioned while retracted), and of sufficient dimension (width and/or length) and rigidity to maintain the retracted nerve in a desired position during surgery. The nerve root retractor 30 may also be equipped with a handle 31 having one or more buttons for selectively applying the electrical stimulation to the stimulation electrode(s) at the end of the nerve root retractor 30. In one embodiment, the nerve root retractor 30 is disposable and the handle 31 is reusable and autoclavable.

Figure 4:
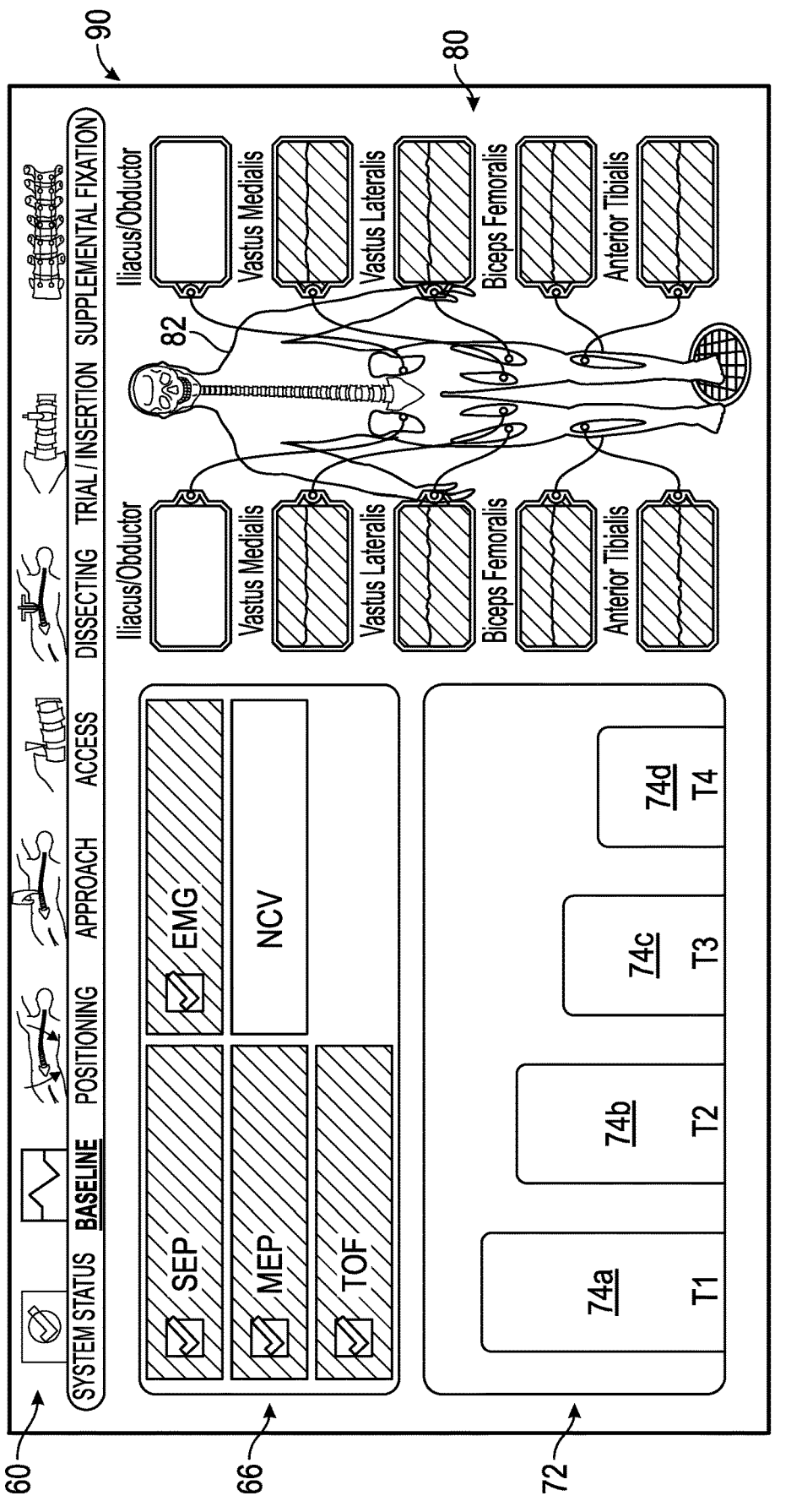
FIG. 4 shows an exemplary baseline status screen generated by the control unit of the surgical system of FIG. 1 in accordance with the present disclosure in which all monitored neural monitoring modalities are acceptable.

FIG. 4 shows an exemplary baseline status screen 90 in accordance with the present disclosure in which all monitored neural monitoring modalities are within the range of predetermined values indicating that the location of the surgical device is acceptable. The baseline status screen 90 is similar to the system status screen 58 which was discussed previously with reference to FIG. 3.

Figure 5:
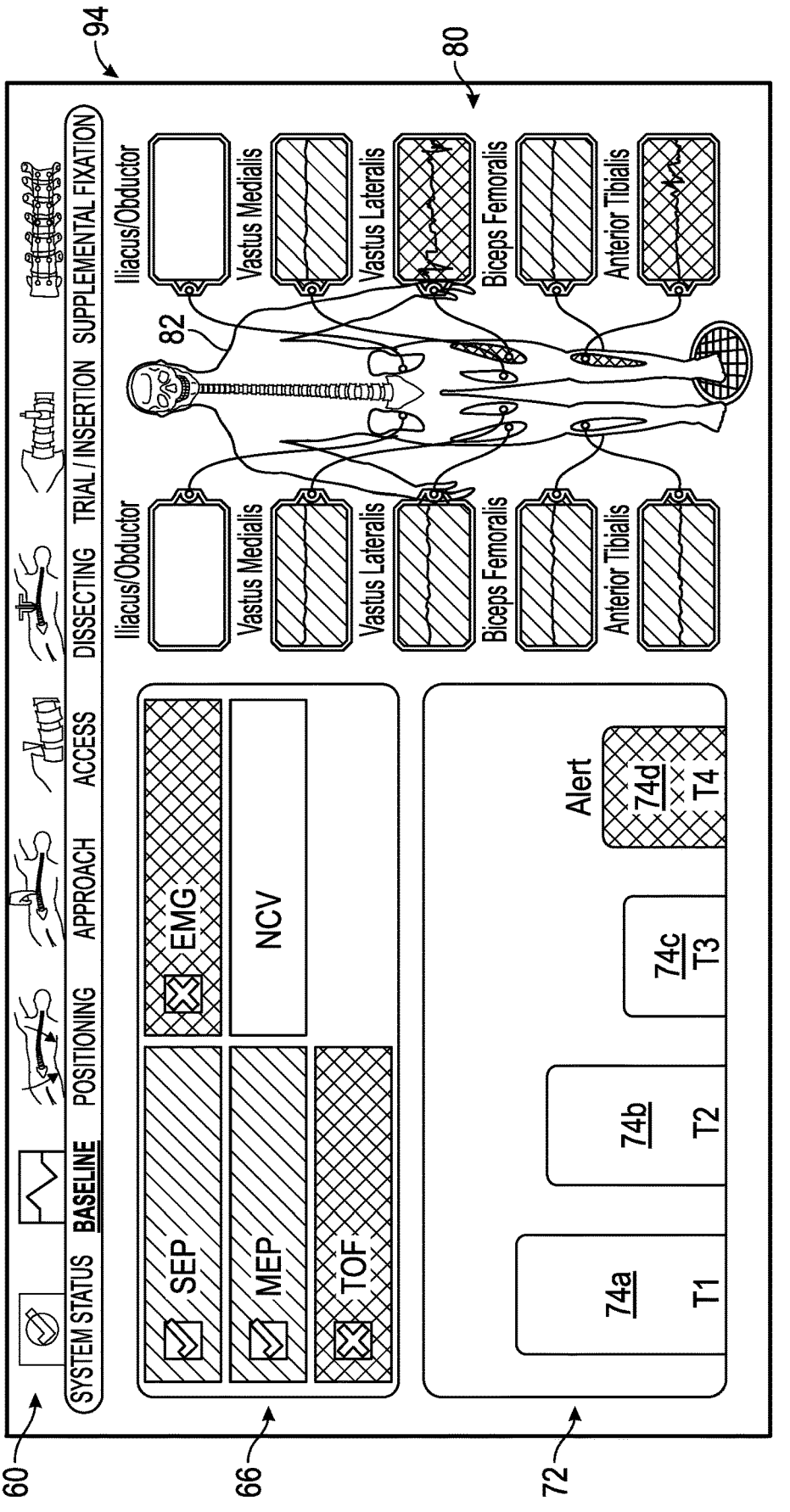
FIG. 5 shows an exemplary baseline status screen generated by the control unit of the surgical system of FIG. 1 in which two of the multiple neural monitoring modalities (e.g., Train of Fours (TOF); and electromyography (EMG)) are indicated as being within an unacceptable range of predetermined values while two of the neural monitoring modalities (e.g., Motor Evoked Potentials (MEP) and somatosensory evoked potential (SSEP)) are indicated as being within an acceptable range of predetermined values.

FIG. 5 shows an exemplary baseline status screen 94 in which two of the multiple neural monitoring modalities (e.g., Train of Fours (TOF); and electromyography (EMG)) displayed within the status summary section 66 are indicated as being within the predetermined range of values indicating an interpretation of being unacceptable while two of the neural monitoring modalities (e.g., Motor Evoked Potentials (MEP) and somatosensory evoked potential (SSEP)) are indicated as being within the predetermined range of values indication an interpretation of being acceptable. Further, an alert is being issued within the anesthetic status section 72 indicating that the level of twitch being sensed by one of electrodes is below the predetermined range of values indicating acceptability. In addition, the monitoring location status section 80 indicates levels being within the predetermined range of values indicating unacceptability are being sensed with respect to the patient's left vastus lateralis nerve, and the patient's left anterior tibialis nerve. The levels shown as being outside the acceptable range of predetermined values may be visualized by utilizing red waveform windows and myotome red highlighting.

Figure 6:
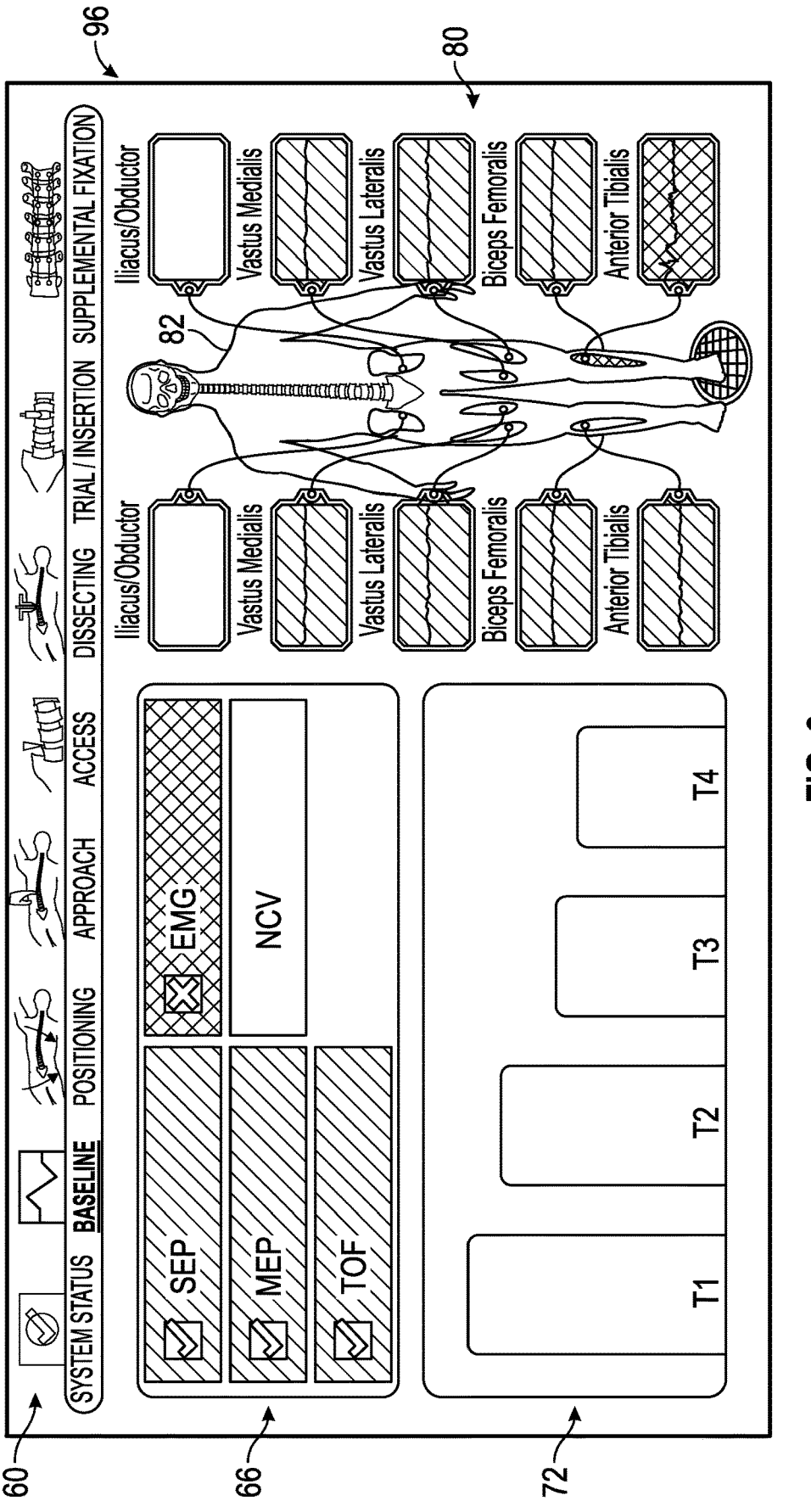
FIG. 6 shows an exemplary baseline status screen generated by the control unit of the surgical system of FIG. 1 in which one of the multiple neuromonitoring modalities (e.g., the electromyography) is indicated as being within an unacceptable range of predetermined values while the other neural monitoring modalities are indicated as being within an acceptable range of predetermined values.

FIG. 6 shows an exemplary baseline status screen 96 in which one of the multiple neural monitoring modalities (e.g., the electromyography) is indicated as being within a predetermined range of values indicating an unacceptable reading while the other neural monitoring modalities within the status summary section 66 are indicated as being within a predetermined range of values indicating an acceptable reading. In addition, the monitoring location status section 80 indicates being within a predetermined range of values indicating that unacceptable levels are sensed with respect to the patient's left anterior tibialis nerve.

Figure 7:
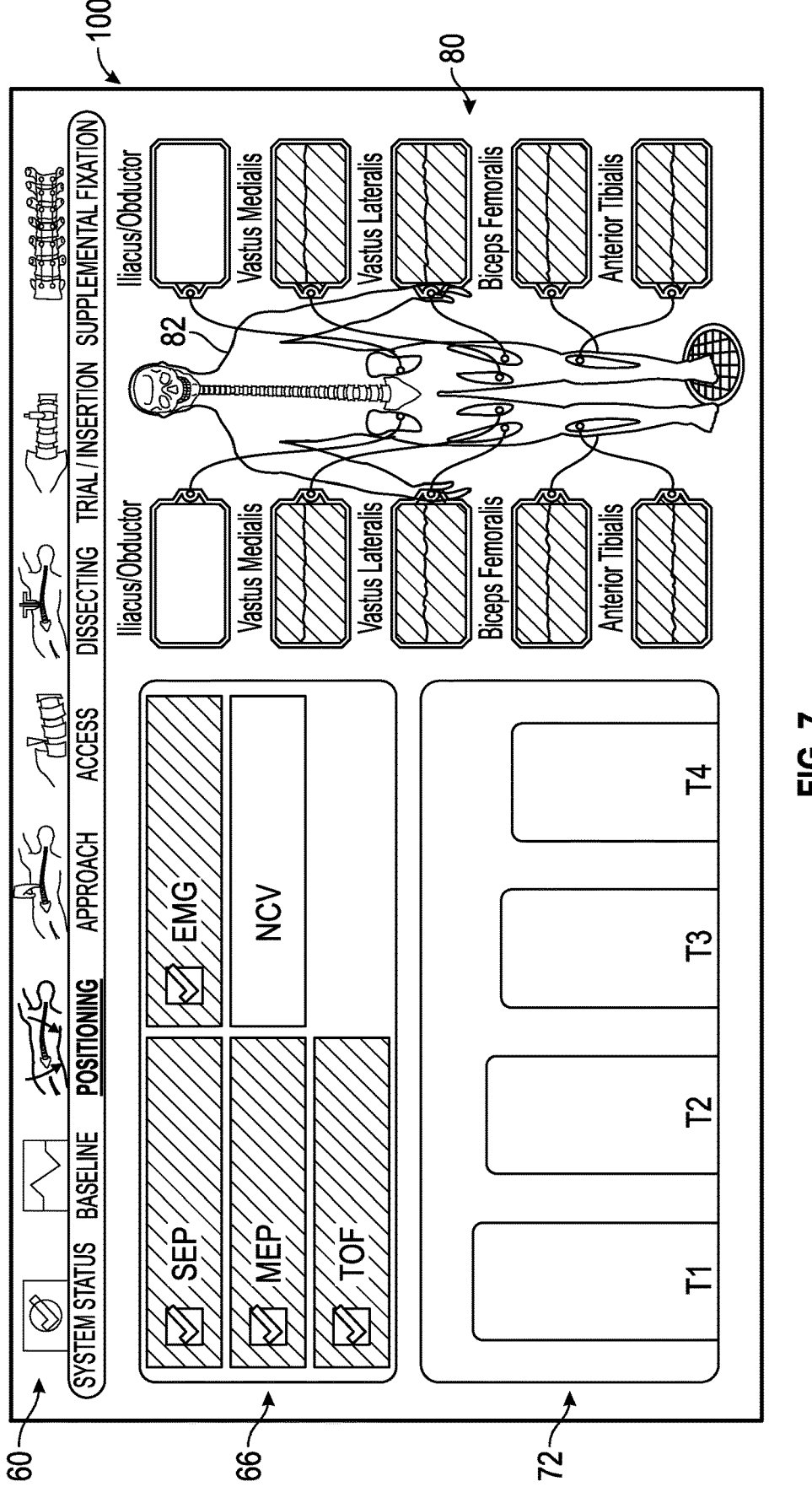
FIG. 7 shows an exemplary positioning status screen generated by the control unit of the surgical system of FIG. 1 in which all of the multiple neural monitoring modalities are indicated as being within an acceptable range of predetermined values.

FIG. 7 shows an exemplary positioning status screen 100 in which all of the multiple neural monitoring modalities are indicated as being within a predetermined range of values indicating an acceptable reading. This is shown for example by utilizing green check marks within the status summary section 66, an absence of red within the anesthetic status section 72, and green waveforms utilized within the monitoring location status section 80.

Figure 8:
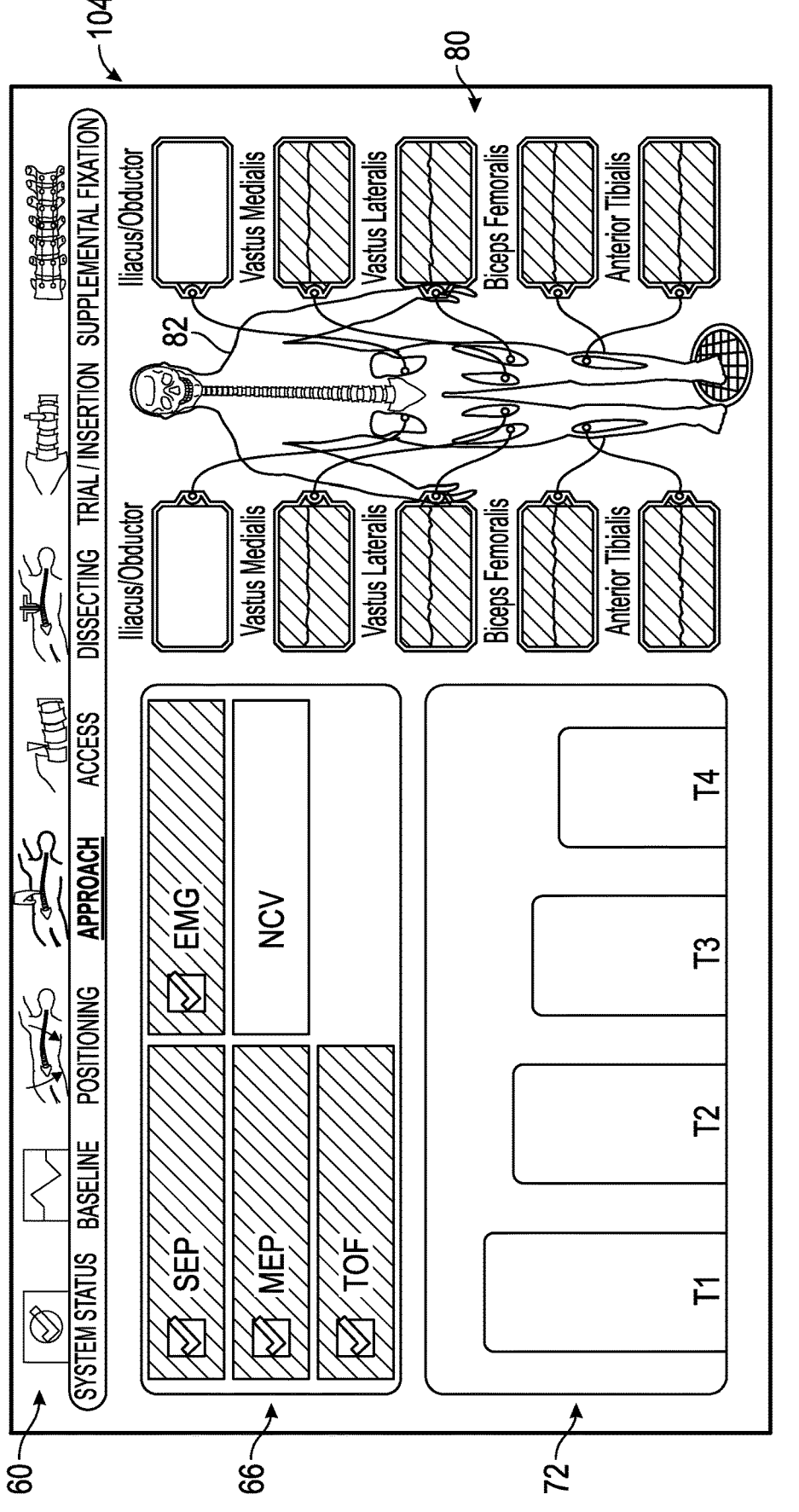
FIG. 8 shows an exemplary approach status screen generated by the control unit of the surgical system of FIG. 1 in which all of the multiple neural monitoring modalities are indicated as being within an acceptable range of predetermined values.

FIG. 8 shows an exemplary approach status screen 104 in which all of the multiple neural monitoring modalities are indicated as being within a predetermined range of values indicating an acceptable reading. The approach status screen 104 is provided when the surgeon system 10 is placed into the approach mode before the surgeon forms an incision within the patient to provide access to the patient's spine.

Figure 9:
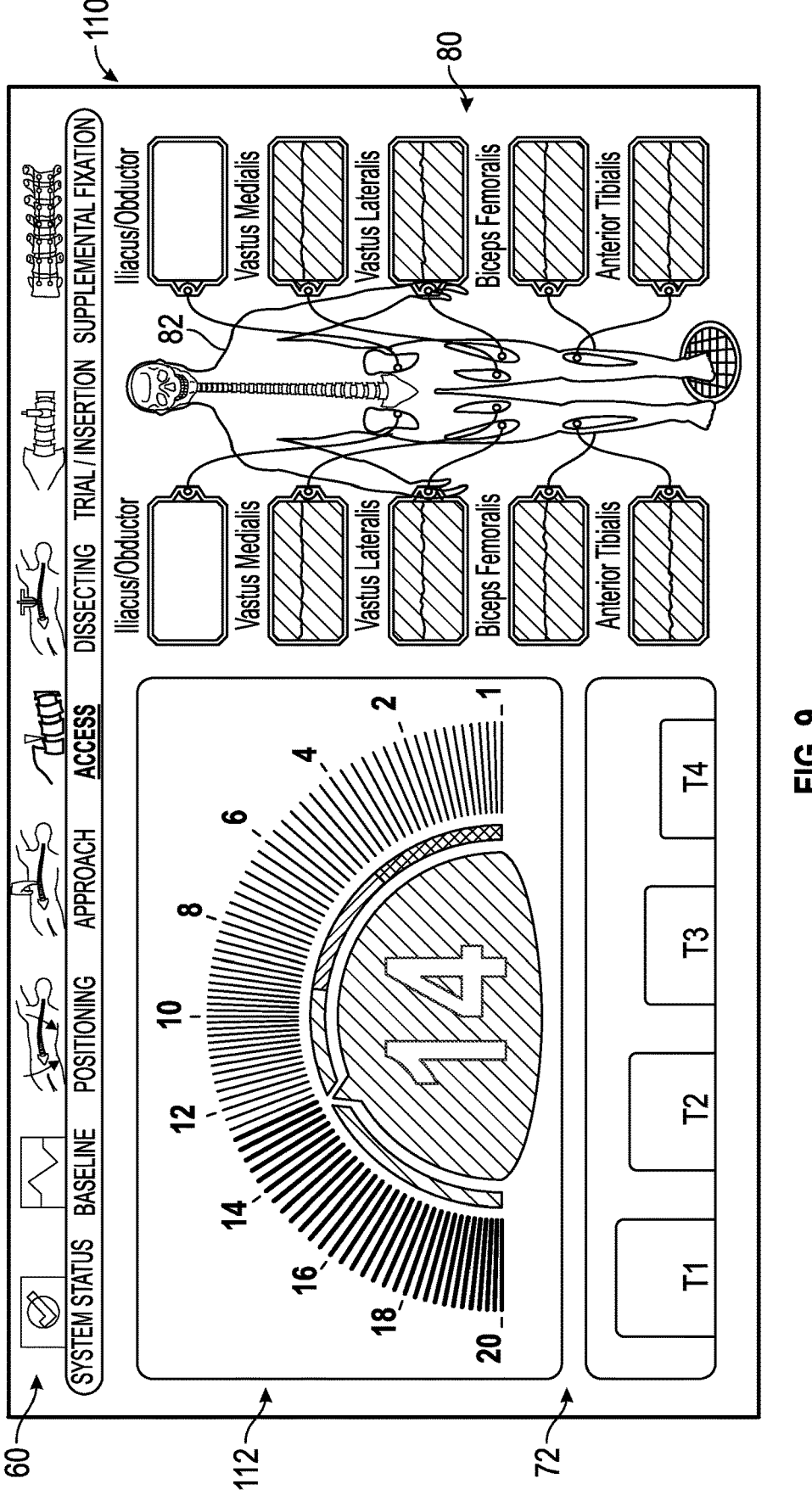
FIG. 9 shows an exemplary access status screen generated by the control unit of the surgical system of FIG. 1 utilized when a surgeon is accessing a patient's spine with a surgical accessory; the access status screen having a nerve proximity screen generated by the control unit of the surgical system of FIG. 1 indicating that the surgical accessory is within a predetermined range of acceptable distances away from the patient's nerves and the other neural monitoring modalities are indicated as being within an acceptable range of predetermined values.

FIG. 9 shows an exemplary access status screen 110 utilized when a surgeon is accessing a patient's spine with a surgical accessory 20; the access status screen 110 having the mode section 60, the anesthetic status section 72, the monitoring location status section 80, and a nerve proximity screen 112 indicating that the surgical accessory 20 is within a predetermined range indicated as being an acceptable distance away from the patient's nerves and the other neural monitoring modalities are indicated as being within a predetermined range of values indicating an acceptable reading.

The nerve proximity screen 112, in one embodiment, displays an amount of current needed to elicit a response from a nerve, in this case 14 mA. It should be noted that the nerve proximity screen 112 may also provide information with respect to the location of the nerve. In particular one or more electrodes can be placed on a side of the surgical accessory 20. In this embodiment, rotation of the surgical accessory 20 will change the location of the electrical stimulus to the patient and thereby provide information with respect to the location of the nerve. In other words, the surgeon may rotate the surgical accessory 20 while monitoring the nerve proximity screen 112 and then note locations where the current needed to elicit the response from the nerve is higher and lower and then use this information to determine the location of the nerve relative to the surgical accessory 20.

Figure 10:
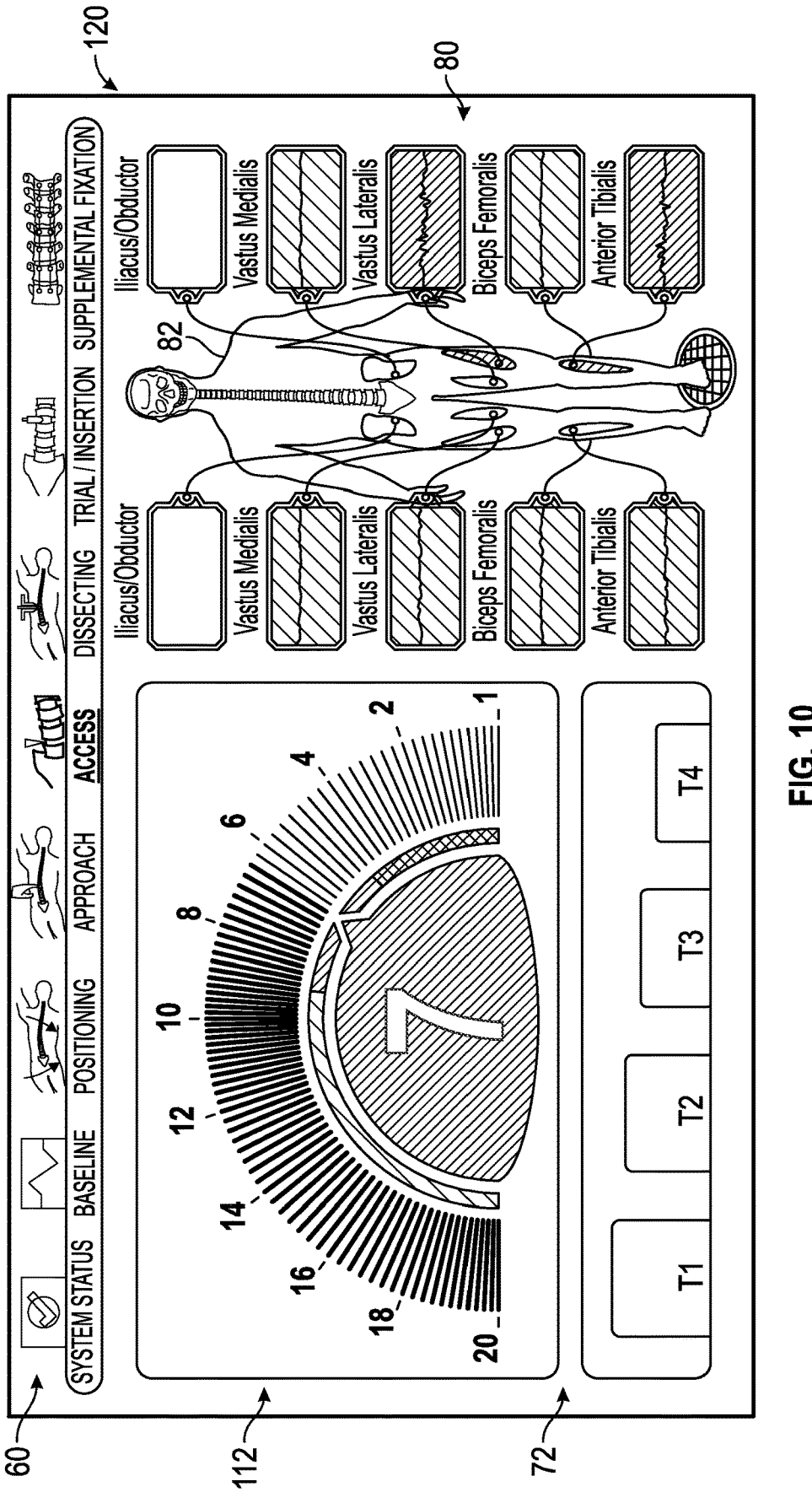
FIG. 10 shows an exemplary access status screen generated by the control unit of the surgical system of FIG. 1 having the nerve proximity screen generated by the control unit of the surgical system of FIG. 1 issuing a visual and/or audible warning to indicate that the surgical accessory is within a predetermined range of acceptable distances away from the patient's nerves, but in close proximity (i.e., closely outside or adjacent to an unacceptable range of predetermined distances) to a vastus lateralis nerve and an anterior tibialis nerve.

FIG. 10 shows an exemplary access status screen 120 having the nerve proximity screen 112 issuing a warning to indicate that the surgical accessory 20 is within a predetermined range of values indicating that the surgical accessory 20 is an acceptable distance away from the patient's nerves and/or other neural structures, but in close proximity to a vastus lateralis nerve and an anterior tibialis nerve. A warning can be shown utilizing any suitable graphics, colors, sounds, smells or the like. In this example, a warning is shown by utilizing a yellow highlighted waveform window in the monitoring location status section 80 as well as the yellow highlighting and lower current (7 mA) needed to elicit response from the nerve. In this case, the surgeon may want to rotate the surgical accessory 20 while monitoring the nerve proximity screen 112 to determine the location of the nerve relative to the surgical accessory 20, and then retract and move the surgical accessory 20 away from the nerve.

Figure 11:
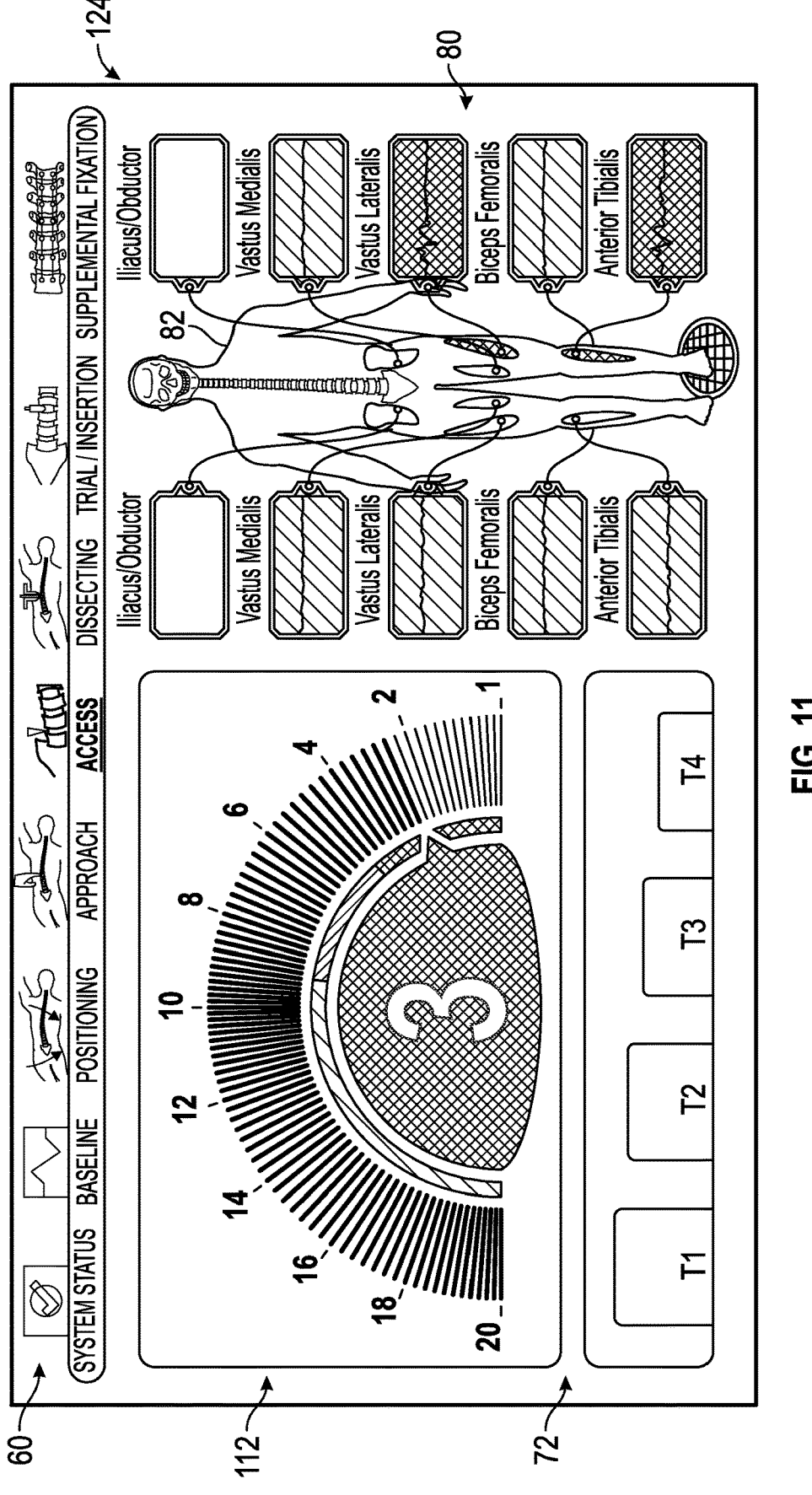
FIG. 11 shows an exemplary access status screen generated by the control unit of the surgical system of FIG. 1 having a nerve proximity screen generated by the control unit of the surgical system of FIG. 1 issuing an audible and/or visual alert due to the surgical accessory being within a predetermined range of unacceptable distances away from the patient's nerves and, in particular, that the surgical accessory is within an unacceptable range of predetermined distances away from the vastus lateralis nerve and the anterior tibialis nerve.

FIG. 11 shows an exemplary access status screen 124 which is similar to the access status screen 120 depicted in FIG. 10 with the exception that the nerve proximity screen 112 of the access status screen 124 is issuing an alert due to the surgical accessory 20 being within a predetermined range of values indicating that the surgical accessory 20 is an unacceptable distance away from the patient's nerves and/or other neural structures and, in particular to the FIG. 11, an unacceptable distance away from the vastus lateralis nerve and the anterior tibialis nerve. The alert is shown by way of example utilizing red highlighting and a lower current (3 mA) needed to elicit a response from the nerve. In this event, the surgeon may want to rotate the surgical accessory 20 while monitoring the nerve proximity screen 112 to determine the location of the nerve relative to the surgical accessory 20, and then retract and move the surgical accessory 20 away from the nerve.

Figure 12:
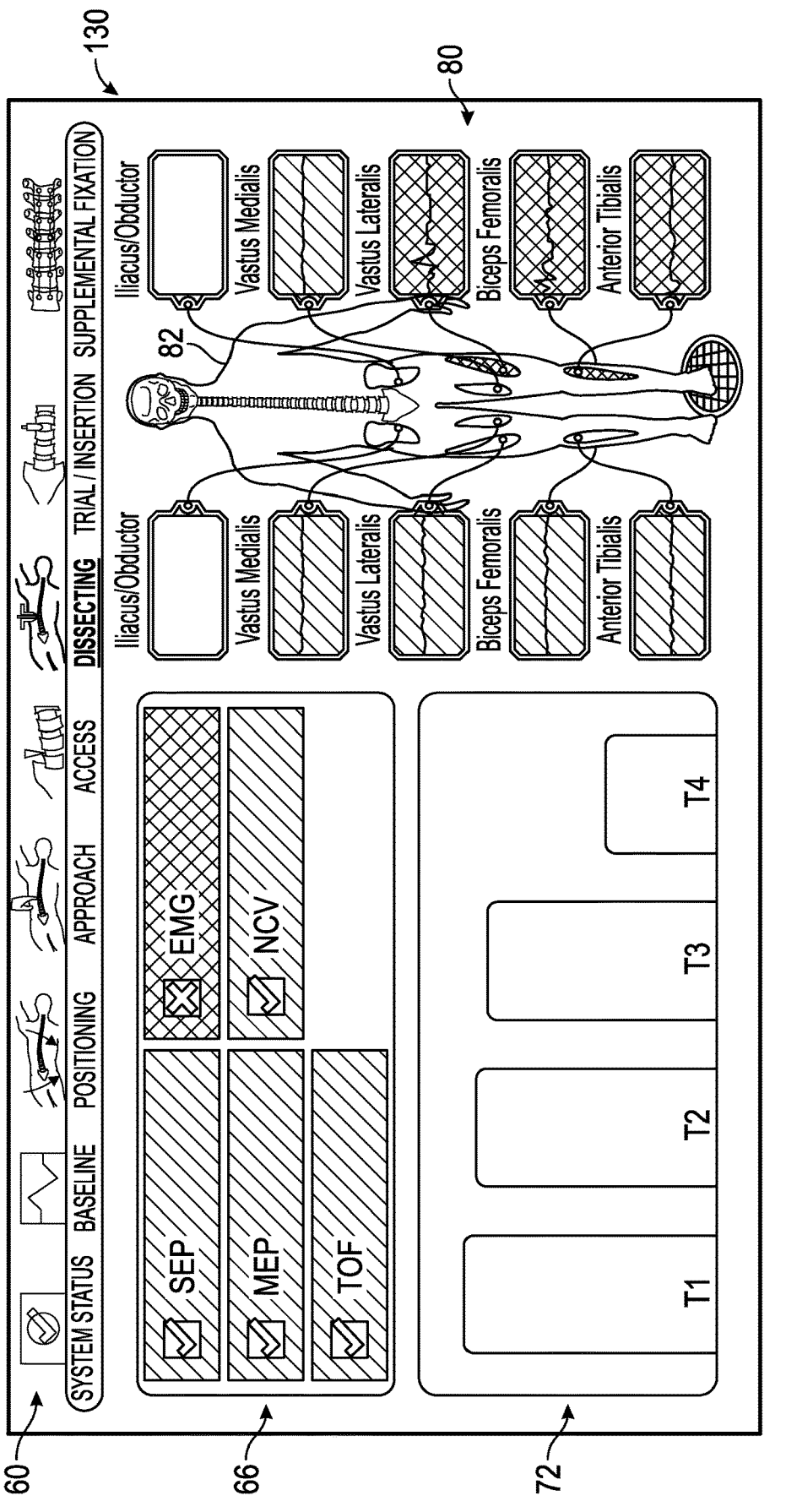
FIG. 12 shows an exemplary dissecting status screen generated by the control unit of the surgical system of FIG. 1 in which a surgical accessory such as a retractor is being utilized by the surgeon and showing (via visual or audible indicia) that one of the multiple neural monitoring modalities is within a predetermined range of unacceptable distances away from a neural structure—e.g., indicating the possible intrusion of the surgical accessory into the vastus lateralis nerve, a biceps femoralis nerve, and/or the anterior tibialis nerve.

FIG. 12 shows an exemplary dissecting status screen 130 which is similar to the system status screen 58, except that the mode section 60 indicates that the surgeon system 10 is placed in the dissecting mode in which a surgical accessory 20 such as a retractor is being utilized by the surgeon and showing that one of the multiple neural monitoring modalities is within a predetermined range of values that is unacceptable and thereby indication that a possible intrusion of the vastus lateralis nerve, a biceps femoralis nerve, and the anterior tibialis nerve has occurred.

Figure 13:
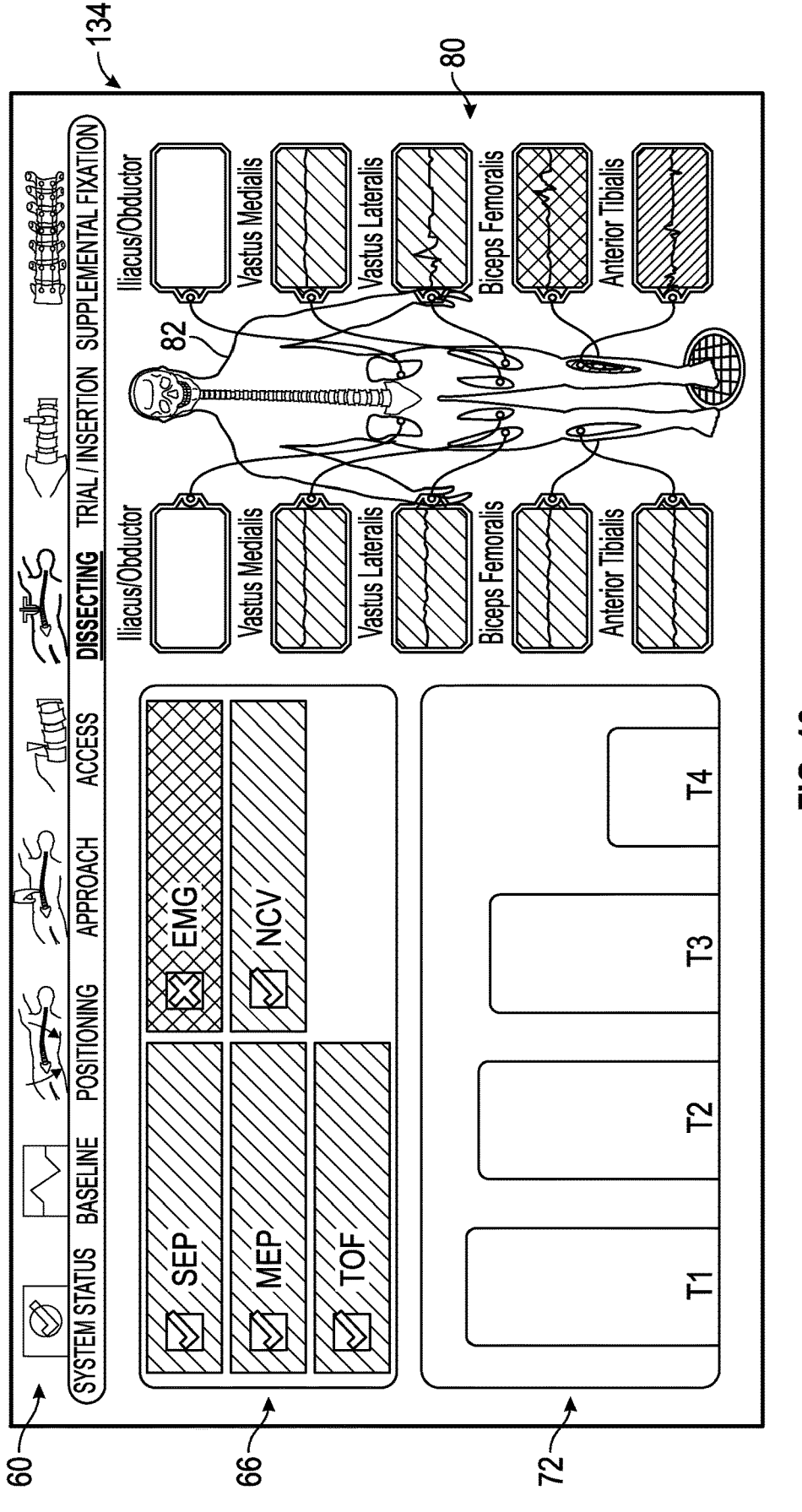
FIG. 13 shows an exemplary dissecting status screen generated by the control unit of the surgical system of FIG. 1 in which a status summary screen of the multiple neural monitoring modalities indicates (via visual or audible indicia) that (i) the SSEP, MEP, TOF, and NCV neural monitoring modalities are within an acceptable range of predetermined values, (ii) the EMG is not within an acceptable range of predetermined, and (iii) a nerve status summary screen generated by the control unit of the surgical system of FIG. 1 indicates via an audible or visual indicia that the surgical accessory is not within an acceptable predetermined range of distances away from a nerve. The exemplary dissecting status screen also indicates a visual warning to the user that the surgical accessory is not within an acceptable predetermined range of distances away from a nerve.

FIG. 13 shows an exemplary dissecting status screen 134 in which a status summary section 66 of the multiple neural monitoring modalities indicates that the SSEP, MEP, TOF, and NCV are all within a predetermined range of values indicating that an acceptable reading while the EMG is indicating that it is within a predetermined range of values indicating that an unacceptable reading is occurring, and a monitoring location status section 80 indicating that with respect to particular nerves and/or other neural structures, the predetermined values being interpreted are either acceptable or not acceptable and issuing a warning with respect to particular nerves where the readings are falling within the predetermined range of values indicating such an unacceptable state.

Figure 14:
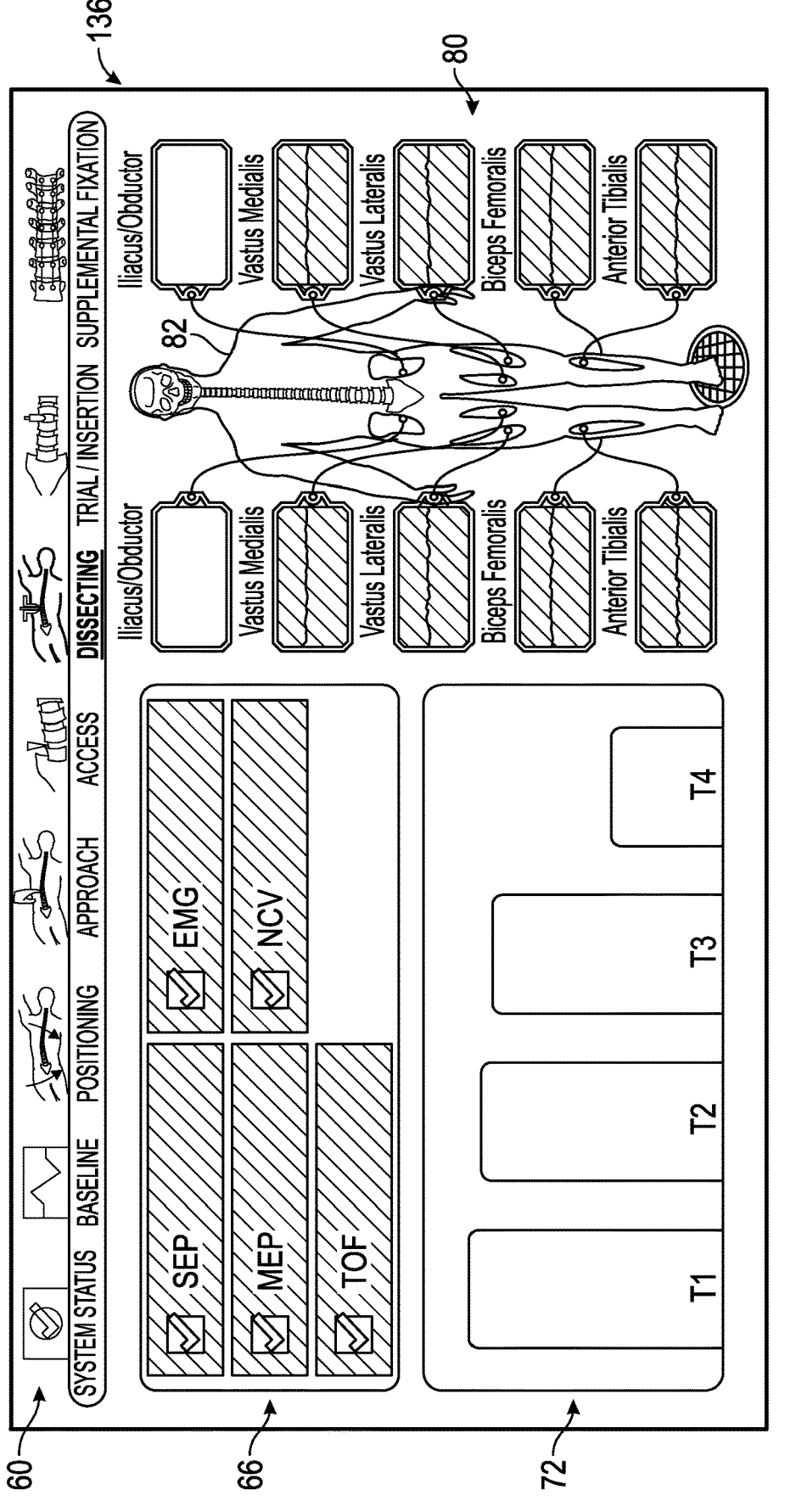
FIG. 14 shows an exemplary dissecting status screen generated by the control unit of the surgical system of FIG. 1 in which all of the multiple neural monitoring modalities are indicated as being within an acceptable range of predetermined values.

FIG. 14 shows an exemplary dissecting status screen 136 which is similar to the dissecting status screen 134 except that all of the multiple neural monitoring modalities are indicated as being within a predetermined range of values indicating an acceptable reading.

Figure 15:
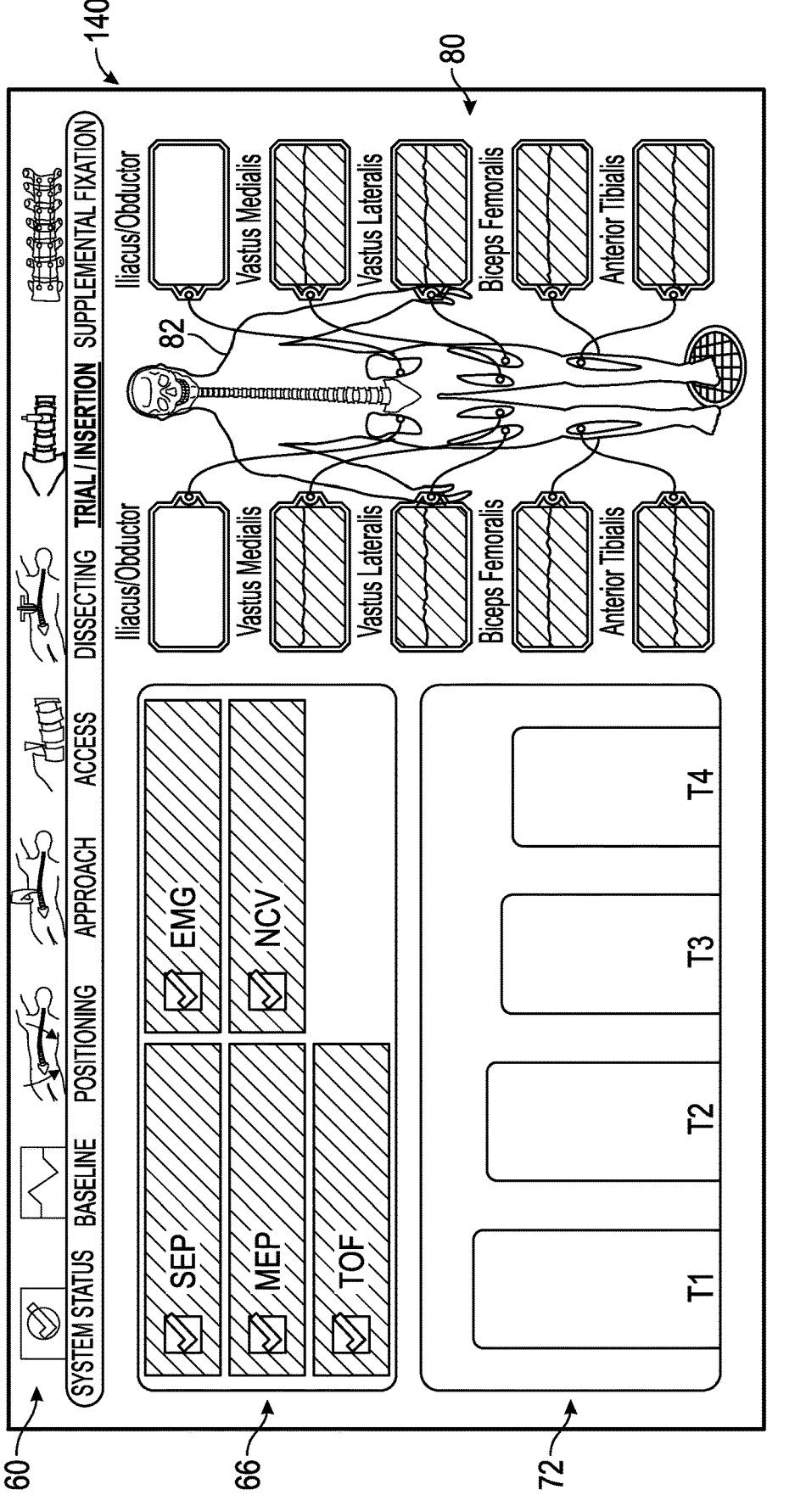
FIG. 15 shows an exemplary trial/insertion screen generated by the control unit of the surgical system of FIG. 1 in which all of the multiple neural monitoring modalities are indicated as being within an acceptable range of predetermined values.

FIG. 15 shows an exemplary trial/insertion screen 140 which is similar to the system status screen 58 which was previously described with reference to FIG. 3. The trial/insertion screen 140 indicates that all of the multiple neural monitoring modalities being monitored are indicated as being within a predetermined range of values indicating an acceptable reading.

Figure 16:
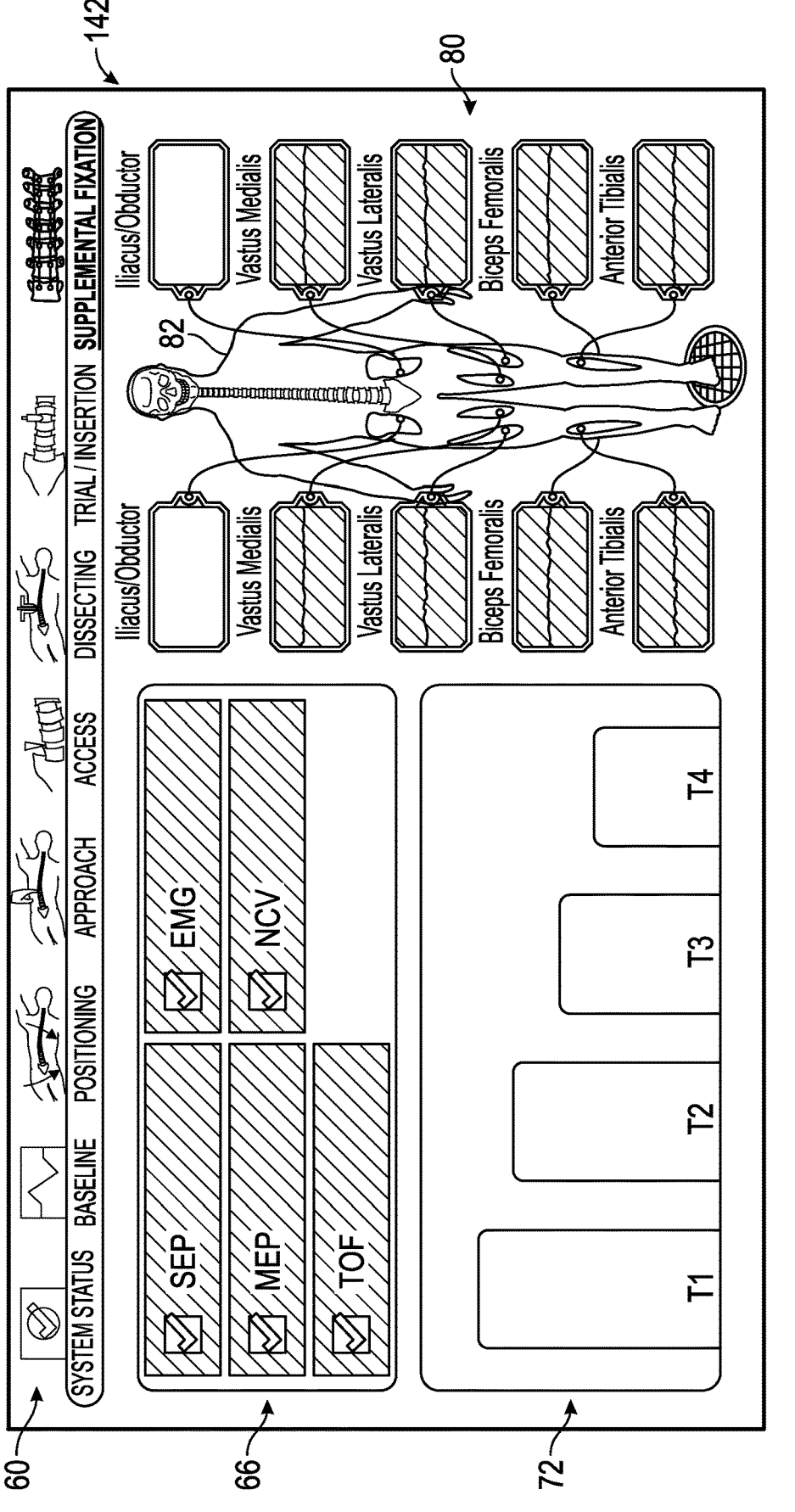
FIG. 16 shows an exemplary supplemental/fixation status screen generated by the control unit of the surgical system of FIG. 1 in which all of the multiple neural monitoring modalities are indicated as being within an acceptable range of predetermined values.
Figure 17A:
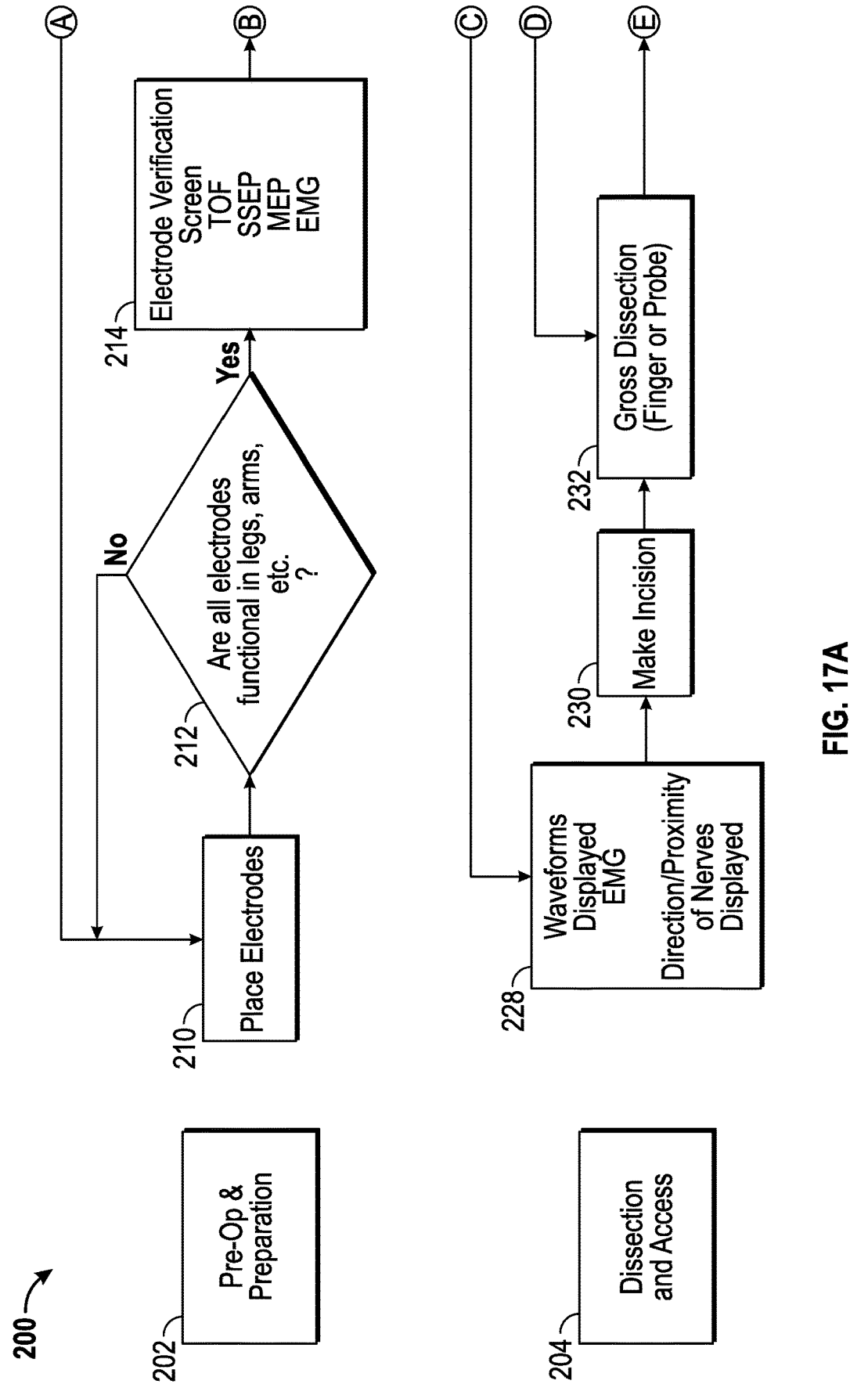
FIGS. 17A, 17B, 17C, 17D, 17E, and 17F collectively show a flow chart illustrating a method for conducting the surgical procedure utilizing the surgical system depicted in FIGS. 1 and 2 according to the present disclosure.
Figure 17B:
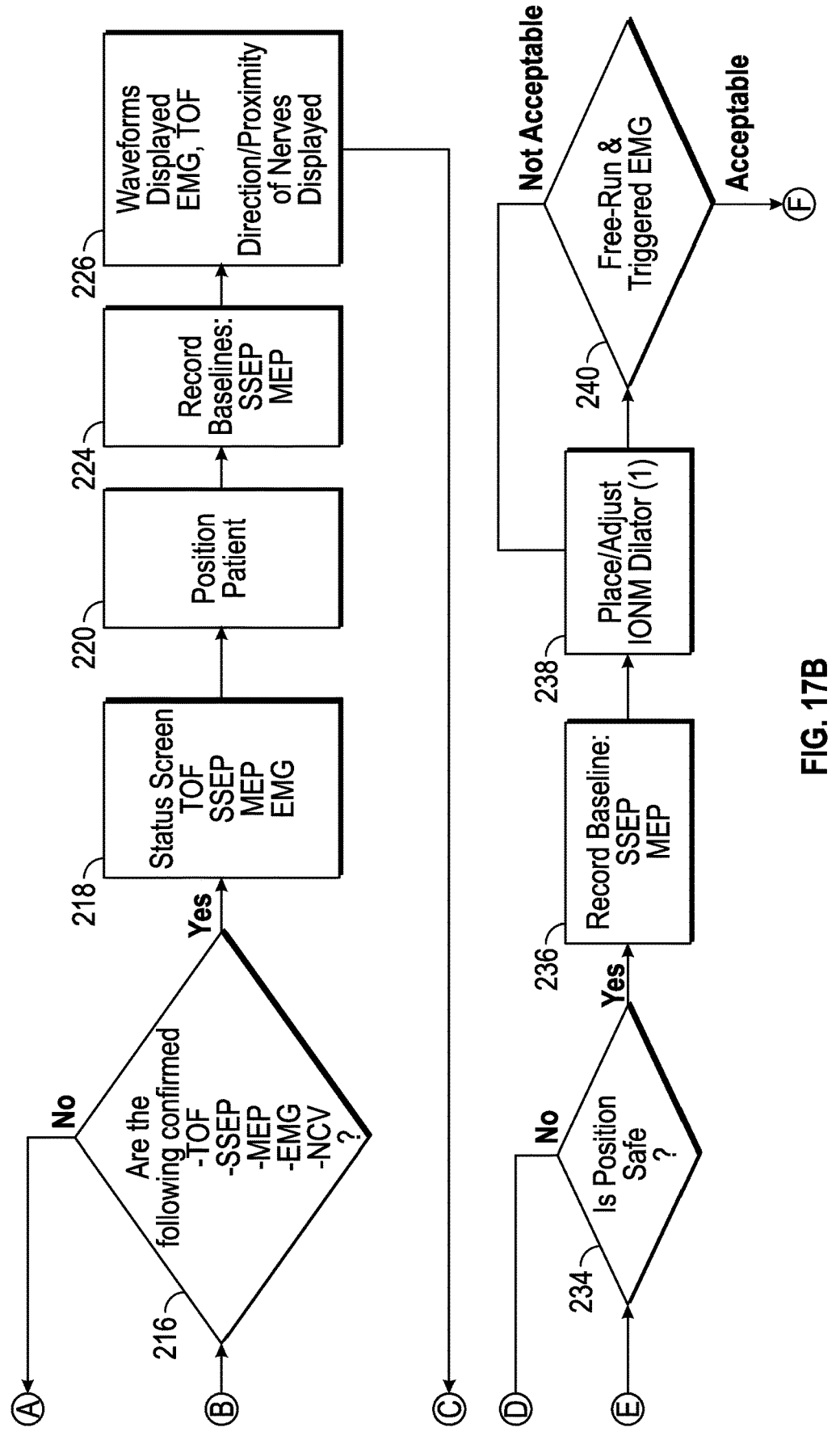
Figure 17C:
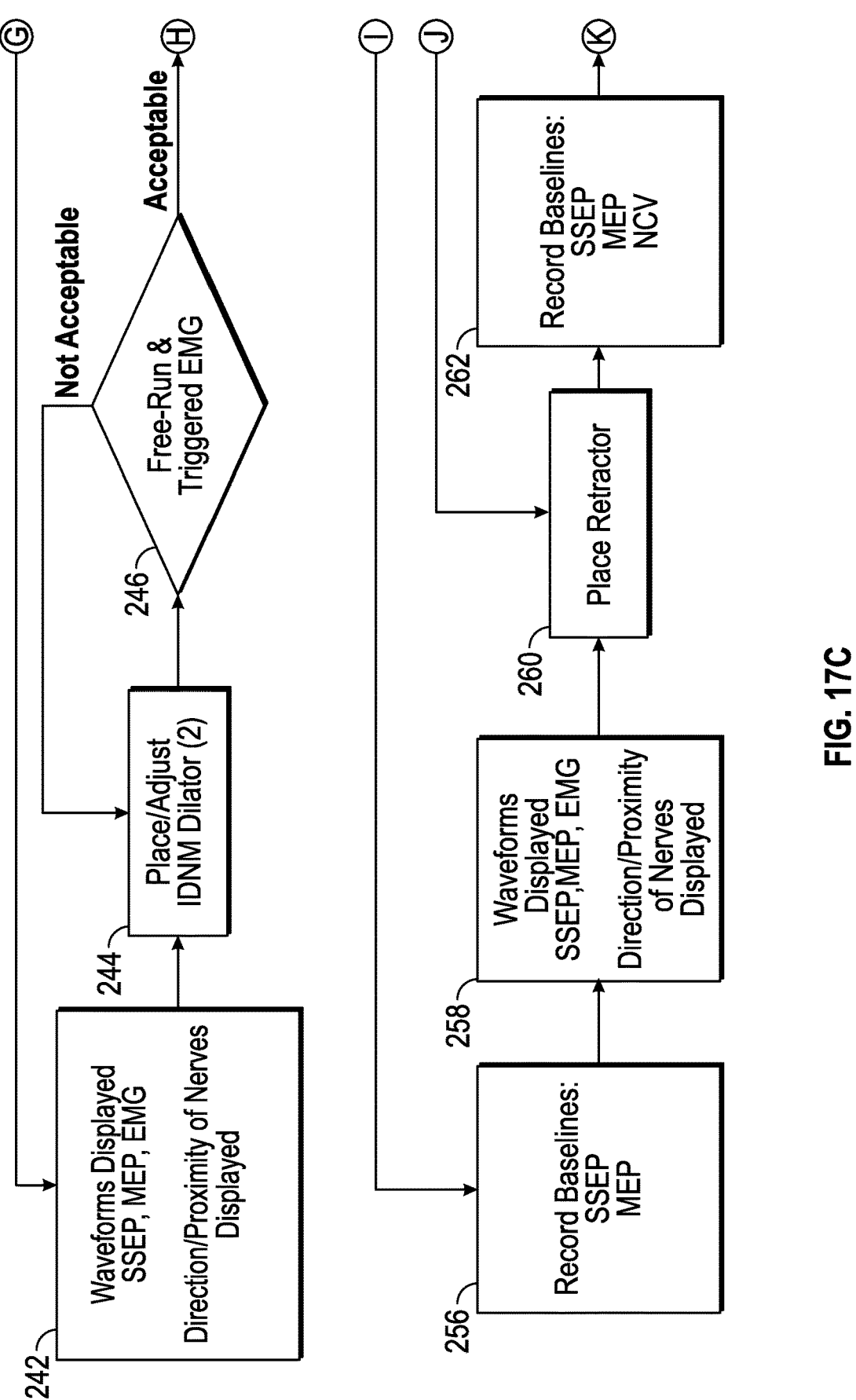
Figure 17D:
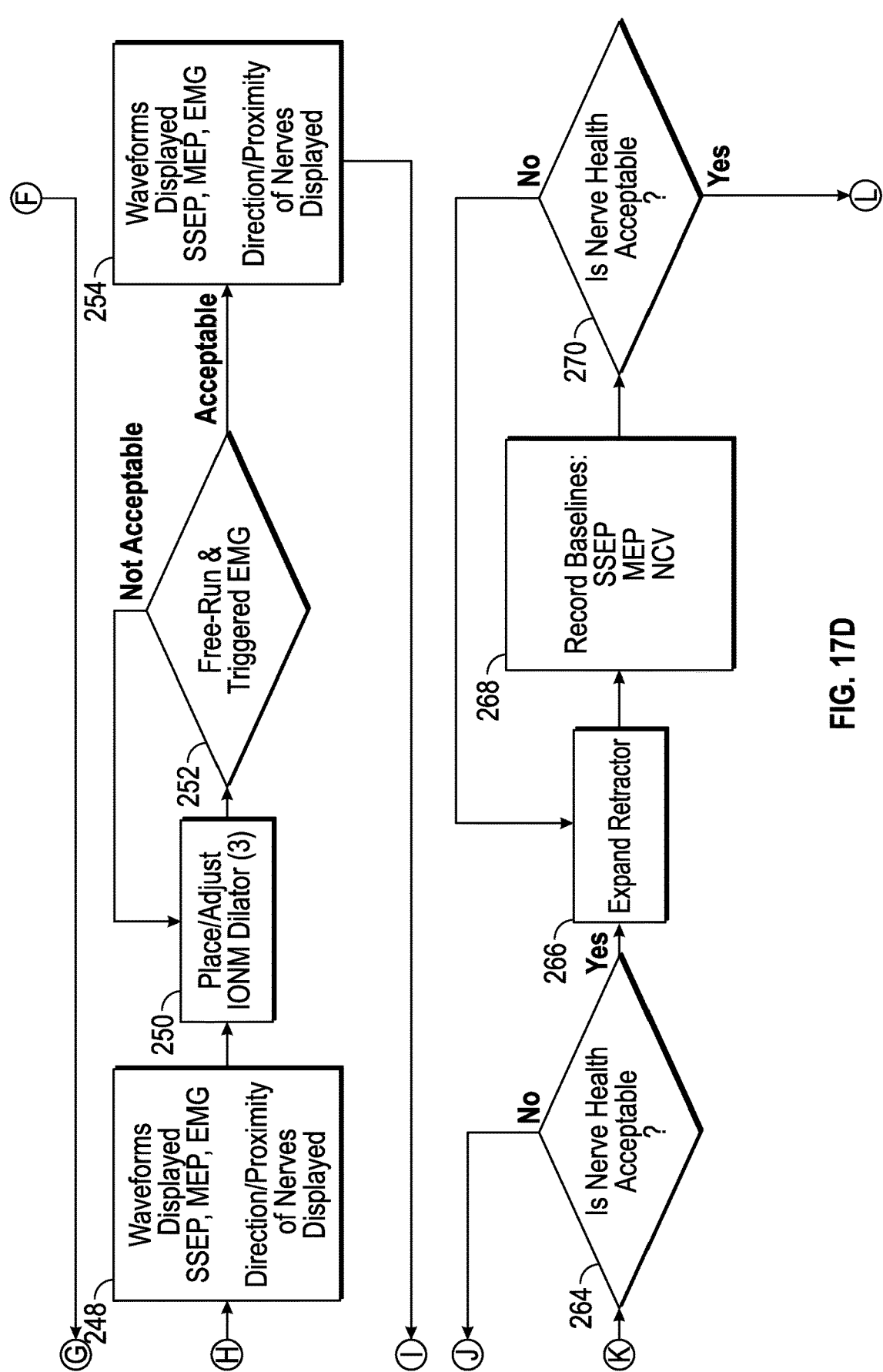
Figure 17E:
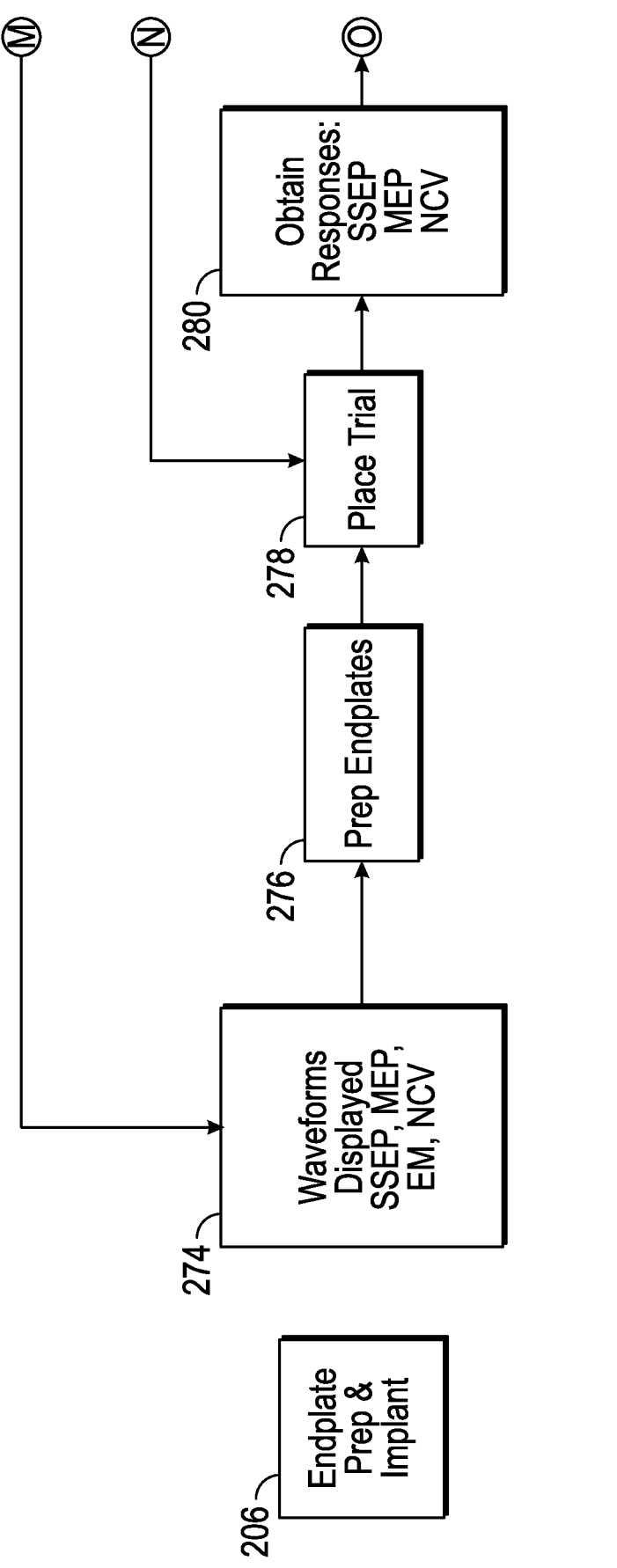
Figure 17F:
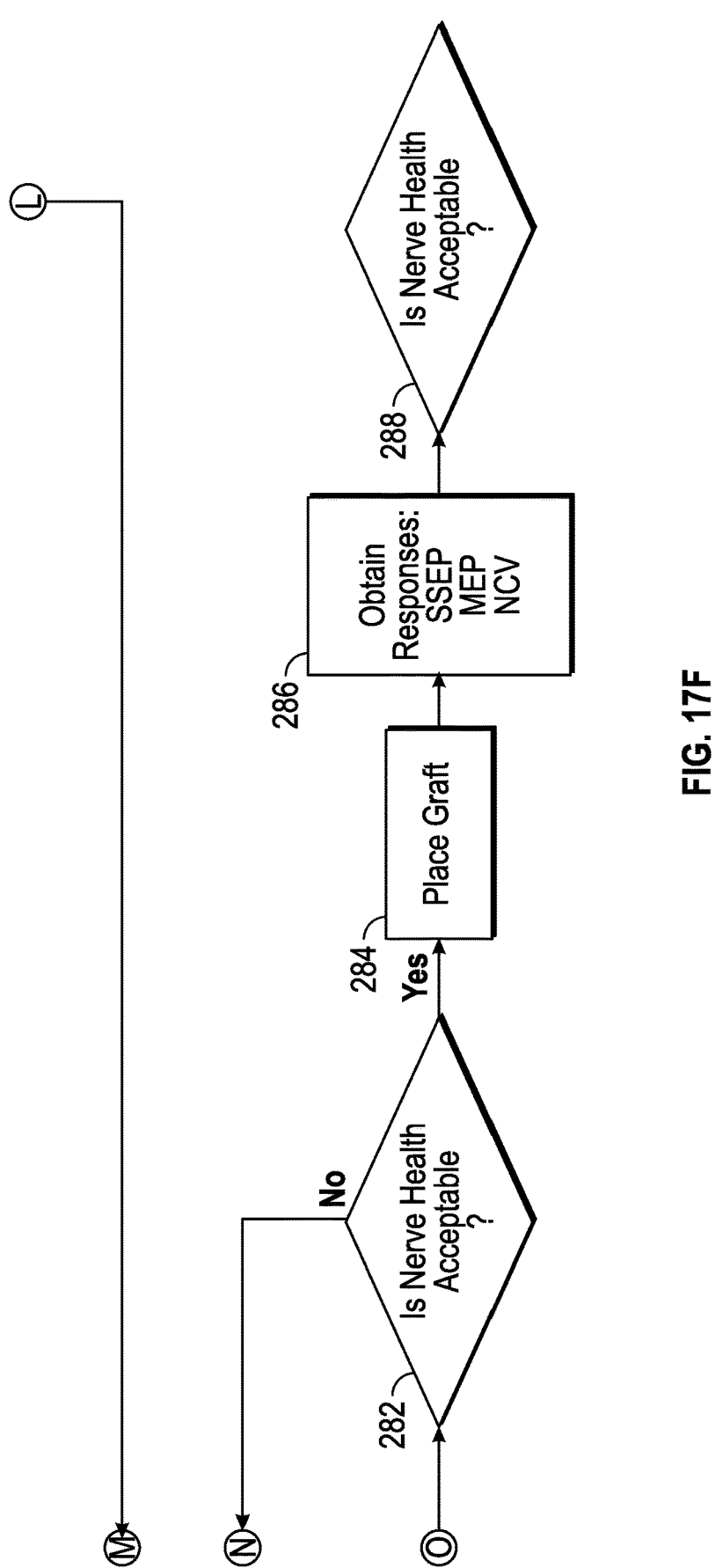

FIG. 16 shows an exemplary supplemental/fixation status screen 142 which is similar to the system status screen 58 which was previously described with reference to FIG. 3. The supplemental/fixation status screen 142 indicates that all of the multiple neural monitoring modalities being monitored are indicated as being within a predetermined range of values indicating an acceptable reading.

FIG. 17 is a flow chart illustrating an exemplary surgical method 200 for conducting a surgical procedure utilizing direct lateral approach to the lumbar spine utilizing the surgical system 10 depicted in FIGS. 1 and 2 according to the presently disclosed and claimed inventive concept(s), process(es), methodology(ies) and/or outcome(s). The surgical method 200 is provided with a preop and preparation section 202, a dissection and access section 204, and an end plate preparation and implant section 206. In general, the surgical method 200 begins with the preop and preparation section 202 and moves sequentially through the dissection and access section 204 and the end plate preparation and implant section 206.

Initially, the surgical method branches to the preop and preparation section 202 in which the peripheral nerve stimulation electrodes 19, the motor evoked potential stimulator 23, the EMG electrodes 34, the anode electrode 35 and the common electrode 37 are placed onto the patient as indicated by a block 210. Then, the processor 12a of the control unit 12 verifies that all of the peripheral nerve stimulation electrodes 19, the motor evoked potential stimulator 23, the EMG electrodes 34, the anode electrode 35, and the common electrode 37 (hereinafter referred to as "electrodes") are positioned correctly and functioning correctly as indicated by a block 212. If the electrodes are functioning correctly, then the preop and preparation section 202 branches to a block 214, and if not, branches back to the block 210 to correct the positioning and functioning of the electrodes.

At the block 214, the processor 12a provides an electrode verification indicia (shown in FIG. 3, for example, as the "check marks" next to each of the SSEP, MEP, TOF and EMG of the status summary section 66) onto the touchscreen display 36 and shows an initial status of the neural monitoring modalities such as TOF, SSEP, MEP, and EMG. The processor 12a, then branches to the block 216 where the surgeon utilizing the surgeon system 10 confirms that the neural monitoring modalities are acceptable. If so, then the processor 12a receives input from the surgeon and then branches to a block 218 to display the system status screen 58 onto the touchscreen display 36. If not, then the processor 12a receives input from the surgeon to branch to the block 210 where any incorrect placement of the electrodes can be corrected.

The positioning mode is then selected on the touchscreen display 36, for example, and then the patient is positioned on a table as indicated by a block 220, preferably in a lateral decubitus position, and then a bolster is placed underneath the patient's hip to aid in opening a space between the patient's 12th rib and the patient's iliac crest. It is also recommended to flex the table to aid in opening the space between the 12th rib and the iliac crest. The patient is then secured to the table in this position.

The processor 12a of the surgical system 10 receives input from the electrodes and records baselines for certain of the neural monitoring modalities, such as SSEP, and MEP as indicated by a block 224. The preop and preparation section 202 then branches to a block 226 where waveforms of the neural monitoring modalities are provided on the touchscreen display 36 by the processor 12a as well as information regarding the direction/proximity of nerves.

As indicated by a block 228, the processor 12a of the surgical system 10 then branches to the dissection and access section 204 where the waveforms of the neural monitoring modalities are provided on the touchscreen display 36 as well as the direction/proximity of nerves. The mode of the surgical system 10 is switched to the approach mode and the surgeon verifies that all of the neural monitoring modalities are acceptable. The surgeon then locates a correct operative level and an incision location preferably utilizing fluoroscopic views and then makes an incision on the skin of the patient preferably targeting an anterior third of the intravertebral disc space as indicated by a block 230. A longitudinal incision may be used if multiple levels will be fused. Once the skin incision is made and subcutaneous tissue is taken down, the oblique muscles of the abdomen should be visible. The surgeon separates the muscle fibers with blunt dissection utilizing either their finger or a probe and enters a retroperitoneal space as indicated by a block 232. The current status of all of the neural monitoring modalities is displayed and the surgeon reviews the touchscreen display 36 to determine whether the position of the finger and/or the probe is safe at a block 234. If so, then the method branches to a step 236 to record baselines of certain of the neural monitoring modalities such as SSEP and MEP. If not, then the method branches to the block 232 where the surgeon may retract the finger or the probe to try a different position.

The surgeon then switches the surgeon system 10 into the access mode, and the surgeon moves the peritoneum anterior with the forefinger or the probe and continues blunt dissection to palpate down to a transverse process and slides forward to the psoas muscle. The surgeon then places the K-wire 25 or the dilator 26 through the psoas muscle to form an initial access passageway to the patient's spine as indicated by a block 238. The processor 12a then utilizes one or more of the neural monitoring modalities such as a free run, NCV and/or a triggered EMG to determine that the K-wire 25 or the dilator 26 are not interfering with any of the nerves and display the current status of the neural monitoring modalities on the touchscreen display 36 as indicated by blocks 240 and 242.

A series of dilators are then placed into the patient to enhance a size of the operative corridor as indicated by blocks 244, 246, 248, 250, 252, and 254 and the current status of the neural monitoring modalities, such as free run, NCV and/or triggered EMG, is displayed on the touch screen display 36 as well as a direction/proximity of nerves as discussed above preferably utilizing the access status screen 110 shown in FIG. 9, for example. The dilators can be either disposable or reusable. Further, the dilators may each include a single electrode, and be formed of aluminum with an insulating coating. The dilators may also include multiple electrodes as discussed in more detail below with reference to FIGS. 18-20.

The method then branches to a block 256 where the surgeon system 10 records baselines for the neural monitoring modalities such as SSEP, NCV and MEP and then provides the current status of the neural monitoring modalities on the touchscreen display 36 preferably using the system status screen 58 shown in FIG. 3 as indicated by a block 258.

The surgeon then switches the mode of the surgeon system 10 to the dissecting mode and places a retractor over the dilators as indicated by a block 260. The surgeon system 10 records baselines of the neural monitoring modalities such as SSEP, MEP and NCV as indicated by block 262. The baselines of the neural monitoring modalities are provided on the touchscreen display 36 and the surgeon determines whether the patient's nerve health is acceptable at a block 264. If not, the method branches to the block 260 where the surgeon removes the retractor and then replaces the retractor within the patient. Once a suitable position for the retractor is located, the retractor is preferably secured in this position with a retractor clamp connected to the table, for example. Once the retractor is secured, the surgeon expands the retractor as indicated at block 266 and then the surgeon system 10 records baselines of the neural monitoring modalities such as SSEP, MEP and NCV at a block 268 and then displays the neural monitoring modalities onto the touchscreen display 36. The surgeon again verifies that the patient's nerve health is acceptable in a block 270 to complete the dissection and access section 204.

The method 200 then branches to a block 274 where the waveforms of the neural monitoring modalities are displayed on the touchscreen display 36. The surgeon verifies that the nerve health is acceptable and then prepares the end plates of the patient's spine utilizing any suitable tools such as a curette and a rasp at a block 276. The surgeon then places a trial spacer between the end plates as indicated by block 278, verifies the position of the trial spacer utilizing a fluoroscope for example and then obtains responses from the neural monitoring modalities such as SSEP, MEP and NCV as indicated by block 280. With respect to NCV, the responses of a segment of a nerve can be monitored with a surgical access instrument described in detail below with reference to FIGS. 18-20, or between an electrode at the surgical target site and another electrode away from the surgical target site. The waveforms of the neural monitoring modalities are displayed on the touchscreen display 36 and the surgeon verifies that the patient's nerve health is acceptable at a block 282. If not, the method 200 branches to the block 278 where the surgeon will then replace or move the trial spacer. Once the trial spacer is properly positioned and the patient's nerve health is determined to be acceptable, then the trial spacer is removed and a graft is placed between the patient's end plates at a block 284. The current status of the neural monitoring modalities is displayed on the touchscreen display 36 at a block 286 and the surgeon verifies that the patient's nerve health is within acceptable predetermined ranges at a block 288.

If the surgery will include supplemental fixation to provide support to the patient's spine, then the surgeon will place the surgeon's system 10 in the supplemental fixation mode. The current status of the neural monitoring modalities is displayed on the touchscreen display 36 while the surgeon connects appropriate hardware to the patient's spine preferably using fluoroscopic techniques to monitor the exact location of the hardware relative to the patient's spine. Common hardware for supplemental fixation includes, but is not limited to, plates, rods and screws that cooperate to provide supplemental support to the patient's spine. If any of the neural monitoring modalities indicates that the hardware is within an unacceptable predetermined distance to any of patient's nerves or other neural structures, then the surgeon's system 10 will issue an alert to the surgeon preferably through visual, olfactory or auditory methodologies. After the hardware is installed, then the surgeon may verify the relative location of the hardware using fluoroscopic techniques, and use the screw test probe 32 to provide an electrical medium to the hardware to obtain additional information regarding the hardware's proximity to any of the nerves. Such information will preferably be shown on the touchscreen display 36 with the current status of the neural monitoring modalities to permit the surgeon to verify that the patient's nerve health is within acceptable predetermined ranges. Thereafter, the surgeon may remove the retractor and close the incision using any appropriate technique known to one of ordinary skill in the art.

Figure 18:
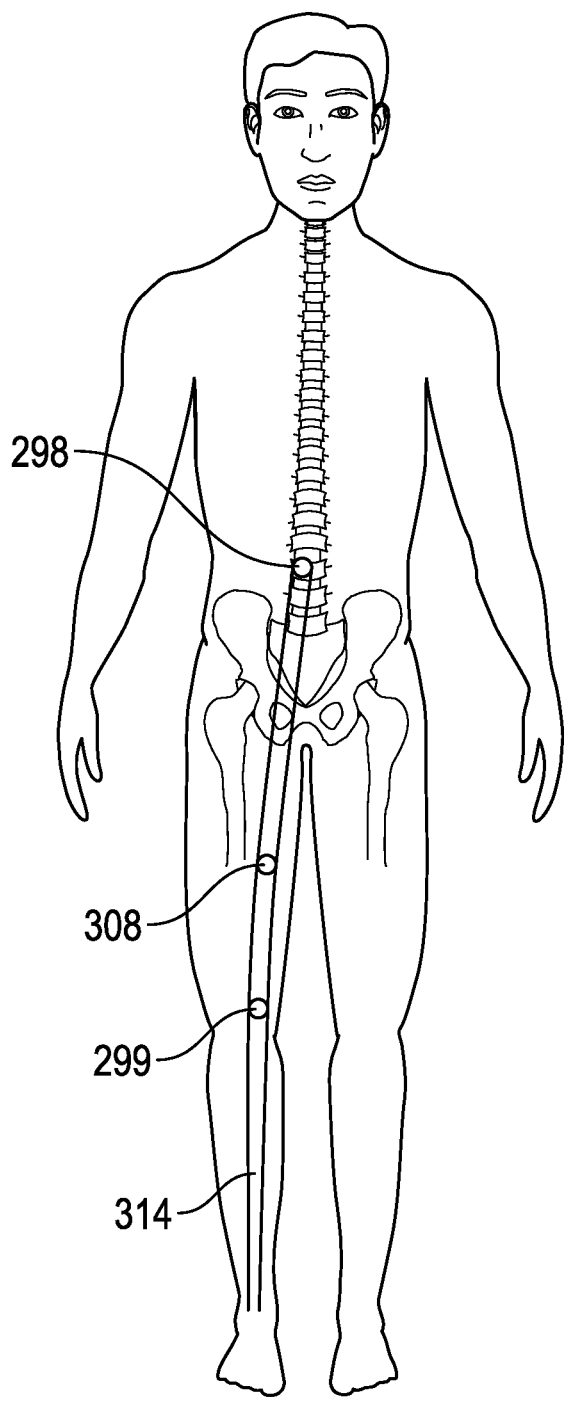
FIG. 18 shows an exemplary patient marked with nerve conduction velocity stimulation/recording sites in accordance with the present disclosure.
Figure 19:
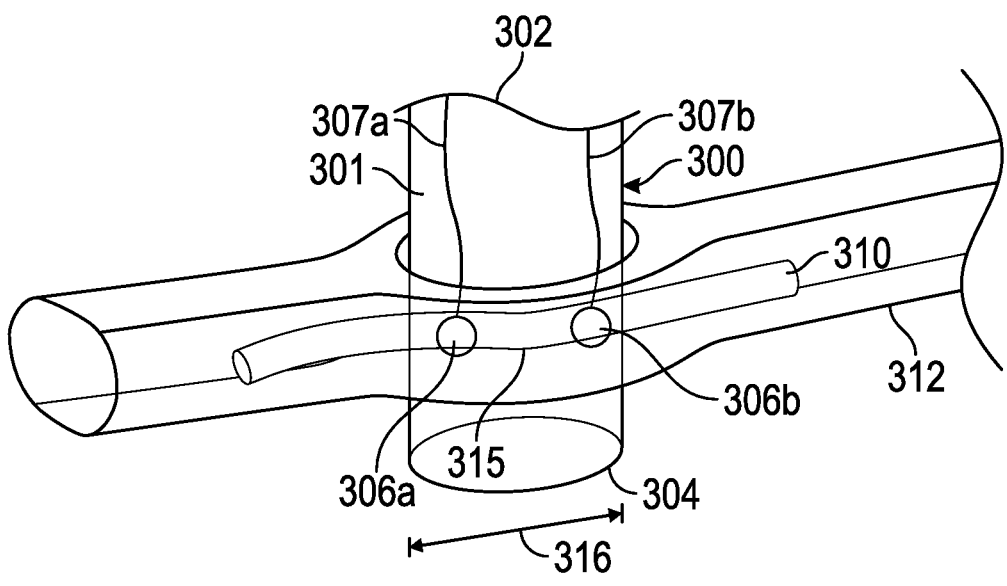
FIG. 19 shows an exemplary surgical access instrument within a psoas muscle being used for nerve conduction velocity measurement in accordance with the present disclosure.

Referring now to FIGS. 18 and 19, in one embodiment, the surgical system 10 can be used to produce NCV measurements within a surgical target site 298; or terminating or originating from the surgical target site 298. To produce NCV measurements in relation to the surgical target site 298, one of the surgical accessories 20 (shown in FIG. 1, for example) may include a surgical access instrument 300 and/or at least one peripheral electrode 299 positioned away from the surgical target site and on a nerve path of a nerve. The surgical access instrument 300 has one or more bodies 301 (with one body 301 being shown and discussed herein by way of example) having a proximal end 302, a distal end 304, and one or more electrodes 306 on the body 301 near the distal end 304. Two electrodes 306a and 306b are shown in FIG. 18 by way of example. The surgical access instrument 300 is also preferably provided with a lead 307 for each electrode 306 so that each electrode 306 can be independently connected to a suitable source of a physical agent, such as a port on the patient module 14. In the example shown, the surgical access instrument 300 is provided with two leads 307a and 307b. The surgical access instrument 300 may be in the form of a probe, dilator, retractor, or any other suitable medical instrument, for example, so long as the surgical access instrument 300 is configured to be placed in the surgical target site 298 and at least one electrode 306 is positioned on or near the distal end 304 for contacting tissue that may contain one or more nerves. The surgical system 10 may also be provided with a ground electrode 308 to facilitate production of NCV measurements, as will be further discussed below.

The electrode 306 may be configured as a stimulating electrode to apply the physical agent to the surgical target site 298 to produce a neural response in a nerve 310 that is proximate to the electrode 306. In other words, the term "proximate" means next to or on the electrode 306 so as to be stimulated and produce the neural response. The electrode 306 may also be configured as a recording electrode to measure the neural response in the nerve 310 produced by the physical agent applied to the patient by a stimulating electrode either at the surgical target site 298 or elsewhere on a nerve path 314 of the nerve 310. The one or more electrode 306 may be partially embedded within the surgical access instrument 300 such that a portion of the one or more electrode 306 remains exposed, may be connected via adhesive, may be formed from flowable epoxy ink, or provided in any other suitable fashion, for example. Where the surgical access instrument 300 is a retractor with a body 301 having one or more blades, the electrode 306 may be partially embedded in or placed on one of the one or more blades as previously described. Further, the one or more electrode 306 may be formed as a part of the body 301 by making the body 301 out of a first material, such as aluminum that is configured to pass the physical agent, and then coating areas of the body 301 that may contact the tissue other than the one or more electrode 306 with a second material configured to block the physical agent.

The one or more peripheral nerve electrodes 299 may be implemented similarly to the plurality of peripheral nerve stimulation electrodes 19, the common electrode 37, the EMG electrodes 34, or the motor evoked potential stimulator 23 described above with reference to FIG. 1. The one or more peripheral nerve electrodes 299 may act as stimulator electrodes or recording electrodes for the purposes of NCV measurements.

In this embodiment, the surgical system 10 may produce NCV measurements by placing the body 301 of the surgical access instrument 300 in a surgical target site 298 near the nerve 310. For example, the surgical target site 298 may be located close to the common peroneal nerve fibers between spinal locations L-4-L-5 and S-1-S-2. It will be understood that the NCV measurements may also be used for the saphenous, genitofemoral, or any other nerve pertinent to a surgical procedure. The body 301 of the surgical access instrument 300 may be placed into tissue, such as a psoas muscle 312, proximate to the nerve 310, such as the peroneal nerve fibers. The one or more peripheral nerve electrodes 299 may have been placed a predetermined distance from the surgical target site 309 and the body 301 of the surgical access instrument 300 along the nerve path 314 formed by the nerve 310, such as the peroneal nerve. The ground electrode 308 may be placed between the surgical access instrument 300 and the one or more peripheral nerve electrodes 299, but is preferably less than 12 inches from the surgical target site 298. The one or more electrodes 306 and the one or more peripheral nerve electrodes 299 may act as stimulating electrodes or recording electrodes along the nerve path 314 of the peroneal nerve, for example. The one or more electrode 306 may also stimulate the nerve 310 allowing the one or more peripheral nerve electrodes 299 to receive electrical signals indicative of a neural response to the stimulation by the electrode 306, with the ground electrode 308 serving to reduce artifacts within the electrical signal produced along the nerve path 314. In this embodiment, the one or more peripheral nerve electrodes 299 receiving the electrical signal allow the surgical system 10 to monitor the nerve conduction velocity of the nerve 310, as described above in combination with the other neural monitoring modalities discussed above. Similarly, the one or more peripheral nerve electrodes 299 may serve as stimulating electrodes and the one or more electrode 306 may serve as the recording electrode. A baseline NCV measurement may be taken at the beginning of the surgical procedure to establish a normal range of NCV for the patient. NCV measurements may occur at predetermined intervals or random intervals during a surgical procedure to ensure that the nerve conduction velocity of nerves 310 that could be affected by the procedure are within a normal range.

Figure 20:
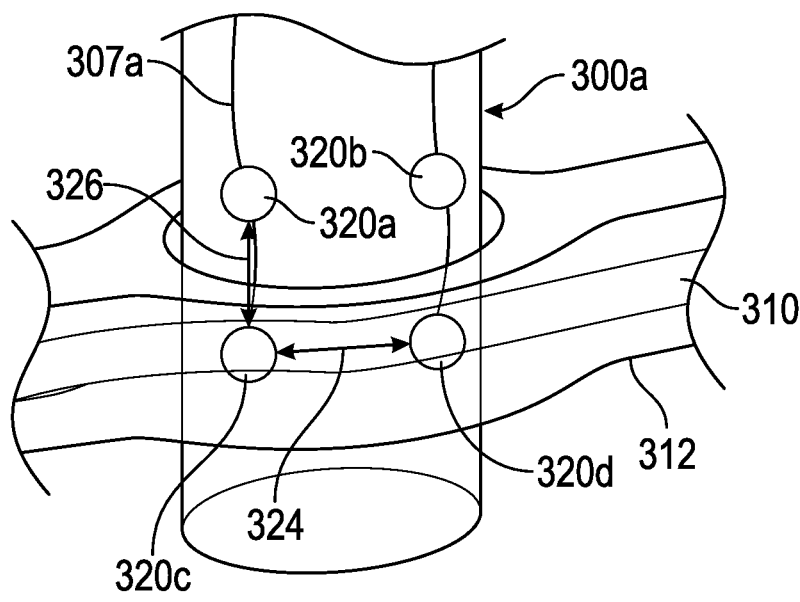
FIG. 20 shows another embodiment of an exemplary surgical access instrument within a psoas muscle being used for nerve conduction velocity measurement in accordance with the present disclosure.

As shown in FIGS. 19 and 20, the surgical access instrument 300 may be provided with two or more electrodes 306a and 306b. With regard to FIG. 19, electrodes 306a and 306b may be used to produce NCV measurements of a segment 315 of the nerve 310 adjacent to the surgical access instrument 300 that is within the surgical target site 309. The electrodes 306a and 306b may be positioned at fixed locations and spaced apart a known distance 316.

The stimulation and recording can be conducted in a bipolar configuration or a monopolar configuration. In a bipolar configuration, the electrodes 306a and 306b are arranged to create the stimulation zone by at least one of the electrodes 306a and 306b applying the physical agent to the segment 313 of the nerve, while another one of the electrodes 306a and 306b is used to receive electrical signals indicative of a neural response to the physical agent to produce NCV measurements. This bi-polar stimulation may be used where nerves and/or the segment 315 are positioned near or between the electrodes 306a and 306b. When using the bipolar configuration, the known distance 316 can be varied based upon a number of factors including the size of the electrodes 306a and 306b, as well as an amount of power used to transmit along the nerve 310. In one embodiment, the known distance 316 can be within a range of 0.5 cm to 2 cm, to create a stimulation zone encompassing the segment 315 of the nerve 310 adjacent to the surgical access instrument 300. In a monopolar configuration, both of the electrodes 306a and 306b may be used to apply the physical agent to the segment 315 of the nerve 310, and the ground electrode 308, separate from the surgical access instrument 300, may receive electrical signals indicative of a neural response to the physical agent. Alternatively, in another monopolar configuration, both of the electrodes 306a and 306b can be used to receive a neural response that is caused by stimulation of the nerve 310 from one of the peripheral electrodes 299. In this case, the electrodes 306a and 306b would receive the neural response at different instants of time, e.g., times T1 and T2, respectively. The difference between the times T1 and T2, and the known distance 316 can be used to measure the nerve conduction velocity of the nerve 310 adjacent to the surgical access instrument 300. To use the monopolar configuration, the distance 316 can be in a range of 0.5 cm to 7.2 cm.

Using two monopolar electrodes 306a and 306b may be advantageous when excessive noise is present in the system due to biological electrical activity. When used in a bipolar configuration, the electrodes 306a and 306b may be more sensitive to the distance 316 and the power used. Also, a bipolar configuration may be more sensitive to local innervation, but may have a narrower electrical measurement range. The control unit 12 may be programmed (e.g., provided with computer executable instructions) to permit the user to use either the monopolar configuration or the bipolar configuration as well as switch between the monopolar configuration and the bipolar configuration.

FIG. 20 shows another embodiment of a surgical access instrument 300a constructed in accordance with the present disclosure. The surgical access instrument 300a may be identical in construction and function as the surgical access instrument 300 describes above, with the exception that the surgical access instrument 300a is provided with more than two electrodes 320. In the example shown, the surgical access instrument is provided with four electrodes 320a, 320b, 320c and 320d that are arranged in a grid formation. However, more electrodes 320 can be provided, and arranged in manners other than a grid formation.

The electrodes 320a and 320b; and 320c and 320d are spaced apart laterally on a body 322 of the surgical access instrument 300a a distance 324. The electrodes 320a and 320c; and 320b and 320d are spaced apart longitudinally on the body 322 a distance 326. The distances 324 and 326 can be the same or different, and such distances 324 and 326 may be known so that the nerve conduction velocity can be determined. Further, the distance between any pair of the electrodes 320a-d may be known so that any two of the electrodes 320a-d can be used to measure the nerve conduction velocity. The plurality of electrodes 314a-314b may be implemented and used similar to electrode 306 and electrodes 306a and 306b. Nerve conduction velocities can be determined using various pairs of the electrodes 320a-d. In this manner, the surgical access instrument 300a can be used to facilitate optimal nerve alignment to the electrodes 320a-d, as well as determine the location and/or the direction of the nerve path 314 of the nerve 310 relative to the location of the body 322 of the surgical access instrument 300a. In other words, the electrodes 320a-d may also facilitate optimal nerve alignment to the electrodes and be operated in pairs to perform NCV measurements.

The surgical access instrument 300 may also be used to generate an F-wave to measure NCV when the electrode 306, the electrodes 306a and 306b, or the plurality of electrodes 314a-314d are in contact or near a motor nerve, in order to measure the NCV of the motor nerve. Additionally, the surgical access instrument 300 may generate an H-wave to stimulate a nerve and record a reflexive electrical discharge from a muscle in a limb, using the one or more peripheral nerve electrodes 299. The afferent impulse, the physical agent produced by the one or more peripheral nerve electrodes 299, may occur in sensory nerves going from a limb to the spinal cord. An efferent impulse, the physical agent produced by the surgical access instrument 300 may occur in motor nerves.

One skilled in the art will recognize that the presently disclosed concepts can be implemented in a variety of manners, such as systems, products, methods and/or kits of component parts grouped together and/or capable of being assembled. For example, in one embodiment, the surgical access instrument 300 or 300a can be grouped together with the control unit 12 and/or the patient module 14 to form a surgical system kit.

The preceding description has been presented with reference to some embodiments. Persons skilled in the art and technology to which this disclosure pertains will appreciate that alterations and changes in the described structures and methods of operation can be practiced without meaningfully departing from the principle, and scope of this application. Accordingly, the foregoing description should not be read as pertaining only to the precise structures described and shown in the accompanying drawings, but rather should be read as consistent with and as support for the following claims, which are to have their fullest and fairest scope.

Furthermore, none of the description in the present application should be read as implying that any particular element, step, or function is an essential element which must be included in the claim scope. The scope of patented subject matter is defined only by the allowed claims. Moreover, none of these claims are intended to invoke paragraph six of 35 USC § 112 unless the exact words "means for" are followed by a participle.

What is claimed is:

1. A method of evaluating nerve function via a plurality of neural monitoring modalities, the method comprising:
   applying a first electrical stimulus within a surgical target site of a patient via a first electrode provided on a surgical access instrument during a surgical procedure;
   providing a second electrical stimulus via a plurality of peripheral electrodes acting as stimulating electrodes, the plurality of peripheral electrodes located apart from the surgical target site and the surgical access instrument;
   monitoring neuromuscular activity of the patient via a plurality of peripheral sensors disposed on the patient for an indication of neuromuscular activity, each peripheral sensor of the plurality of peripheral sensors being one of: a recording peripheral electrode of the plurality of peripheral electrodes and a mechanical sensor, the recording peripheral electrode being a particular peripheral electrode of the plurality of peripheral electrodes acting as a recording electrode;
   determining a nerve conduction velocity (NCV) measurement based on reception of the second electrical stimulus within the surgical target site by a second electrode applied on the surgical access instrument, and the indication of neuromuscular activity from one or more of the plurality of peripheral sensors;
   providing an indication via a display if the NCV measurement is within a predefined range;

detecting a neuromuscular response from the indication of neuromuscular activity, the neuromuscular response comprising at least one of a somatosensory evoked potential (SSEP) response; a motor evoked potential (MEP) response; a spontaneous electromyography (EMG) response, a triggered EMG response, or a mechanomyography (MMG) response; and providing an indication of the detected neuromuscular response via the display.

2. The method of claim 1, further comprising determining a minimum electrical current for the first electrical stimulus provided by the surgical access instrument that is required to elicit a sensed neuromuscular response from at least one of the plurality of peripheral sensors.

3. The method of claim 1, wherein the surgical access instrument comprises a nerve root retractor having a curved distal end portion with a concave inner surface, and wherein the first electrode is disposed on the concave inner surface; the method further comprising:

contacting a nerve root of a nerve with concave inner surface, and wherein the applied first electrical stimulus is applied directly to the nerve via the first electrode.

* * * * *